US012622698B2

(12) United States Patent
Gagner et al.

(10) Patent No.: US 12,622,698 B2
(45) Date of Patent: May 12, 2026

(54) SYSTEM AND METHOD FOR RETRIEVING A MAGNETIC IMPLANT FOR FORMING AN ANASTAMOSIS IN THE DIGESTIVE TRACT

(71) Applicant: GT METABOLIC SOLUTIONS, INC., Wilmington, DE (US)

(72) Inventors: Michel Gagner, Montréal (CA); Todd A. Krinke, Buffalo, MN (US); Thierry Thaure, San Jose, CA (US); Ted Schmitz, St. Louis Park, MN (US)

(73) Assignee: GT METABOLIC SOLUTIONS, INC., Wilmington, DE (US)

( * ) Notice: Subject to any disclaimer, the term of this patent is extended or adjusted under 35 U.S.C. 154(b) by 0 days.

(21) Appl. No.: 18/944,940

(22) Filed: Nov. 12, 2024

(65) Prior Publication Data

US 2025/0152172 A1     May 15, 2025

Related U.S. Application Data

(60) Provisional application No. 63/598,261, filed on Nov. 13, 2023.

(51) Int. Cl.
A61B 17/11 (2006.01)
A61B 17/00 (2006.01)

(52) U.S. Cl.
CPC ..................... A61B 17/1114 (2013.01); *A61B 2017/00876* (2013.01)

(58) Field of Classification Search
CPC ...... A61B 17/1114; A61B 2017/00876; A61B 2017/1139
See application file for complete search history.

(56) References Cited

U.S. PATENT DOCUMENTS 5,830,224 A * 11/1998 Cohn ................. A61B 17/3207
                                                        606/167
9,943,355 B2 4/2018 Babini et al.
2008/0091264 A1* 4/2008 Machold .............. A61M 25/09
                                                        623/2.1
2008/0108860 A1 5/2008 Bell et al.
(Continued)

FOREIGN PATENT DOCUMENTS

WO       2022133421 A1     6/2022

*Primary Examiner* — Alexander J Orkin
(74) *Attorney, Agent, or Firm* — The Belles Group, P.C.

(57) ABSTRACT

Systems, devices and methods for retrieving a magnetic implant used for forming a magnetic compression anastomosis between two adjacent walls of hollow organs of the digestive system of a patient are provided. The retrieving of the magnetic implant can be done using a retrieving device configured to magnetically engage the magnetic implant. The retrieving device can include a flexible housing comprising a housing wall defining a retriever magnet receiving cavity and a plurality of retriever magnets provided in series within the retriever magnet receiving cavity. The flexible housing can include a proximal portion having a proximal stopper engageable with a delivery wire. The proximal stopper can include a delivery attachment engageable with the delivery wire. The retrieving device can be magnetically engageable with the magnetic implant within the digestive tract when brought in sufficiently close proximity of each other via manipulation of the delivery wire.

22 Claims, 31 Drawing Sheets

(56)                    References Cited

U.S. PATENT DOCUMENTS

| | | | |
|---|---|---|---|
| 2009/0125042 A1* | 5/2009 | Mouw ................. | A61B 17/1114 |
| | | | 606/153 |
| 2010/0222664 A1* | 9/2010 | Lemon ................. | A61M 25/09 |
| | | | 600/407 |
| 2011/0144560 A1* | 6/2011 | Gagner ............... | A61B 17/1114 |
| | | | 604/8 |
| 2011/0218476 A1* | 9/2011 | Kraemer ........... | A61M 25/0068 |
| | | | 604/8 |
| 2012/0035628 A1* | 2/2012 | Aguirre ............... | A61B 17/1114 |
| | | | 606/153 |
| 2013/0197306 A1* | 8/2013 | Armand ............ | A61M 25/0138 |
| | | | 604/95.04 |
| 2013/0317375 A1* | 11/2013 | Garcia ............... | A61B 18/1492 |
| | | | 600/508 |
| 2014/0052107 A1 | 2/2014 | Voeller et al. | |
| 2015/0057687 A1 | 2/2015 | Gittard et al. | |
| 2016/0089515 A1* | 3/2016 | Hansen ................. | A61M 25/09 |
| | | | 604/528 |
| 2016/0256230 A1* | 9/2016 | Kowshik ................ | A61B 34/35 |
| 2017/0333052 A1* | 11/2017 | Ding ................ | A61B 17/00234 |
| 2018/0243536 A1* | 8/2018 | von Segesser .. | A61M 25/09025 |
| 2018/0280039 A1 | 10/2018 | Sun | |
| 2019/0060612 A1* | 2/2019 | Besselink ......... | A61M 25/0051 |
| 2019/0274687 A1* | 9/2019 | Wang ................. | A61B 17/1114 |
| 2020/0138438 A1* | 5/2020 | Harrison ............. | A61B 17/1114 |
| 2022/0087678 A1* | 3/2022 | Gagner ............... | A61B 17/1114 |
| 2022/0192671 A1 | 6/2022 | Gagner et al. | |
| 2024/0023965 A1 | 1/2024 | Harrison et al. | |

* cited by examiner

SYSTEM AND METHOD FOR RETRIEVING A MAGNETIC IMPLANT FOR FORMING AN ANASTAMOSIS IN THE DIGESTIVE TRACT

RELATED APPLICATION

This application claims the benefit of U.S. Provisional Application No. 63/598,261 filed on Nov. 13, 2023, which is incorporated herein by reference in its entirety.

TECHNICAL FIELD

The technical field generally relates to medical techniques for treating digestive tract conditions. In particular, the technical field relates to medical techniques for retrieving a magnetic implant for forming an anastomosis in the digestive tract.

BACKGROUND

Digestive surgeries and medical procedures to treat conditions associated with the digestive tract, diabetes and obesity often require alteration of the digestive tract through incisions, sutures, punctures and/or stapling, which can cause trauma to the organ being altered and lead to bleeding. For instance, bariatric surgery procedures can be used to treat obesity, and can be aimed at bypassing a portion of the stomach and/or the intestine. Other examples of such digestive surgeries can involve forming an anastomosis between selected organs of the digestive system for various medical purposes, such as the oesophagus, the stomach, the intestines, the biliary tract, the pancreas, the colon and the rectum. Such medical procedures can lead to an increased risk of infection or other complications.

Magnetic compression anastomosis can be used in the context of medical procedures to treat conditions associated with the digestive tract. With magnetic compression anastomosis, necrosis is induced in tissue sandwiched between two magnets. A healing process takes place around the magnets, while the compressed tissue eventually dies and separates from surrounding living tissue. The magnets are released along with the necrotic tissue, leaving an open passage known as an anastomosis.

There remain a number of challenges with respect to surgery procedures in the digestive tract, particularly with respect to the formation of anastomoses and the devices used to assist in the formation of anastomoses.

SUMMARY

In accordance with an aspect, there is provided a retrieving device for insertion within a digestive tract of a patient, the retrieving device comprising:
- a flexible housing having a proximal portion engageable with a delivery wire and a distal portion opposite the proximal portion, the flexible housing comprising:
  - a housing wall defining a retriever magnet receiving cavity; and
- a plurality of retriever magnets provided in series within the retriever magnet receiving cavity;
- wherein the retrieving device is magnetically engageable with a first magnetic implant of a pair of magnetic implants configured for forming an anastomosis between two adjacent walls of the digestive tract of the patient.

In some implementations, the housing wall of the flexible housing defines retriever housing slots extending laterally around a portion of the housing wall.

In some implementations, the flexible housing is tubular, and the housing wall of the flexible housing defines retriever housing slots extending circumferentially around a portion of the housing wall.

In some implementations, longitudinally adjacent ones of the retriever housing slots are provided in an offset configuration.

In some implementations, the retriever housing slots comprise:
- a first set of retriever housing slots provided spaced-apart from each other and extending along a first arc of the flexible housing; and
- a second set of retriever housing slots provided spaced-apart from each other and extending along a second arc of the flexible housing, the first and second sets of the retriever housing slots being longitudinally spaced-apart from one another.

In some implementations, the first set of retriever housing slots comprises a first pair of retriever housing slots and the second set of retriever housing slots comprises a second pair of retriever housing slots.

In some implementations, a first retriever housing slot of the first pair of retriever housing slots extends from about 10 o'clock to about 2 o'clock and a second retriever housing slot of the first pair of retriever housing slots extends from about 4 o'clock to about 8 o'clock.

In some implementations, a first retriever housing slot of the second pair of retriever housing slots extends from about 1 o'clock to about 5 o'clock and a second retriever housing slot of the second pair of retriever housing slots extends from about 7 o'clock to about 11 o'clock.

In some implementations, the retriever housing slots of the first set of retriever housing slots extend between about 60% and about 80% of the first arc of the flexible housing.

In some implementations, the retriever housing slots of the second set of retriever housing slots extend between about 60% and about 80% of the second arc of the flexible housing.

In some implementations, the flexible housing comprises a flexible material.

In some implementations, the flexible material comprises a polymeric material.

In some implementations, the polymeric material comprises one or more of silicon and rubber.

In some implementations, the flexible housing comprises a non-flexible material.

In some implementations, the non-flexible material comprises a metal.

In some implementations, the metal comprises one or more of stainless steel and titanium.

In some implementations, the flexible housing comprises a flexible joint.

In some implementations, the flexible joint comprises a coil, is bellow-shaped or comprises a flexible material.

In some implementations, the flexible housing comprises a first portion upstream of the flexible joint and a second portion downstream of the flexible joint, the flexible joint being provided in a central region of the flexible housing.

In some implementations, at least one of the first and second portions of the flexible housing comprises a non-flexible material.

In some implementations, the flexible housing is shaped a coil.

In some implementations, the retriever magnets are shaped as substantially spherical beads or have a cylindrical shape.

In some implementations, the retriever magnets are distributed within the retriever magnet receiving cavity to define a non-magnetic portion and a magnetic portion of the retrieving device.

In some implementations, a length ratio between a length of the magnetic portion and a length of the non-magnetic portion is between about 10:1 to about 2:1.

In some implementations, a length ratio between a length of the magnetic portion and a length of the non-magnetic portion is about 4:1.

In some implementations, the retrieving device further comprises a distal plug at the distal portion of the flexible housing, the distal plug being engageable with the distal portion of the flexible housing to maintain the plurality of retriever magnets within the retriever magnet receiving cavity.

In some implementations, the flexible housing comprises inwardly extending distal protrusions configured to engage the distal plug.

In some implementations, the retrieving device further comprises a distal plug at a distal portion of the flexible housing, the distal plug being integral with the distal portion of the flexible housing to maintain the plurality of retriever magnets within the retriever magnet receiving cavity.

In some implementations, the distal plug has atraumatic features.

In some implementations, the distal plug is dome-shaped.

In some implementations, the retrieving device further comprises a proximal stopper at the proximal portion of the flexible housing, the proximal stopper being engageable with the proximal portion of the flexible housing to maintain the plurality of retriever magnets within the retriever magnet receiving cavity.

In some implementations, the flexible housing comprises inwardly extending proximal protrusions configured to engage the proximal stopper.

In some implementations, the retrieving device further comprises a proximal stopper at the proximal portion of the flexible housing, the proximal stopper being integral with the flexible housing to maintain the plurality of retriever magnets within the retriever magnet receiving cavity.

In some implementations, the proximal stopper is engageable with the delivery wire.

In some implementations, the proximal stopper comprises a delivery attachment engageable with the delivery wire.

In some implementations, the retrieving device is magnetically engageable with the first magnetic implant by contacting a main surface of the first magnetic implant.

In some implementations, a magnetic strength of the plurality of retriever magnets is selected such that a magnetic attraction between the retrieving device and the first magnetic implant enables displacement of the first magnetic implant along the digestive tract of the patient.

In some implementations, the delivery wire is connected to a handle manipulable by a healthcare provider.

In accordance with another aspect, there is provided a system for retrieving a first magnetic implant of a pair of magnetic implants configured for forming an anastomosis between two adjacent walls of a digestive tract of a patient, the system comprising:

a retrieving device for insertion within a digestive tract of a patient, the retrieving device comprising:
a flexible housing having a proximal portion and a distal portion opposite the proximal portion, the flexible housing comprising:
a housing wall defining a retriever magnet receiving cavity;
a plurality of retriever magnets provided in series within the retriever magnet receiving cavity; and
a delivery wire engageable with the proximal portion of the flexible housing; and
a handle engageable with the delivery wire;
wherein the retrieving device is magnetically engageable with the first magnetic implant of the pair of magnetic implants within the digestive tract when brought in sufficiently close proximity of each other via manipulation of the delivery wire.

In some implementations, the system further comprises one or more features as defined herein.

In some implementations, the delivery wire comprises a delivery wire inner core and a delivery wire outer shell.

In accordance with another aspect, there is provided a system for forming an anastomosis between two adjacent walls of a digestive tract of a patient, the system comprising:
first and second magnetic implants configured to magnetically couple to each other through the two adjacent walls of the digestive tract at a desired site of the anastomosis to compress a portion of the two adjacent walls therebetween and form a necrotic area that becomes surrounded by a scarred edge following a healing time period; and
a retrieving device for insertion within a digestive tract of a patient, the retrieving device comprising:
a flexible housing having a proximal portion engageable with a delivery wire and a distal portion opposite the proximal portion, the flexible housing comprising:
a housing wall defining a retriever magnet receiving cavity;
a plurality of retriever magnets provided in series within the retriever magnet receiving cavity;
wherein the retrieving device is magnetically engageable with a first magnetic implant of a pair of magnetic implants configured for forming an anastomosis between two adjacent walls of the digestive tract of the patient.

In some implementations, the system further comprises one or more features as defined herein.

In accordance with another aspect, there is provided a retrieving device for insertion within a digestive tract of a patient, the retrieving device comprising:
a housing having a proximal portion engageable with a delivery wire and a distal portion opposite the proximal portion, the housing comprising:
a housing wall defining a retriever magnet receiving cavity;
a retriever magnet provided in series within the retriever magnet receiving cavity;
wherein the retrieving device is magnetically engageable with a first magnetic implant of a pair of magnetic implants configured for forming an anastomosis between two adjacent walls of the digestive tract of the patient.

In some implementations, the retrieving device further comprises one or more features as defined herein.

In accordance with another aspect, there is provided a method for retrieving a magnetic implant of a pair of magnetic implants configured for forming an anastomosis between two adjacent walls of a digestive tract of a patient, the method comprising:

navigating the magnetic implant into the digestive tract in direction of a location on one side of a desired anastomose site;

introducing a retrieving device into the digestive tract of the patient, a positioning of the retrieving device being modifiable by a healthcare provider via a delivery wire engaged with the retrieving device;

magnetically coupling the magnetic implant with the retrieving device; and displacing the magnetic implant magnetically coupled with the retrieving device via the delivery wire along the digestive tract.

In some implementations, navigating the magnetic implant into the digestive tract in direction of a location on one side of a desired anastomose site is performed endoscopically, laparoscopically or percutaneously.

BRIEF DESCRIPTION OF THE DRAWINGS

The attached figures illustrate various features, aspects and implementations of the technology described herein.

DETAILED DESCRIPTION

Figure 1:
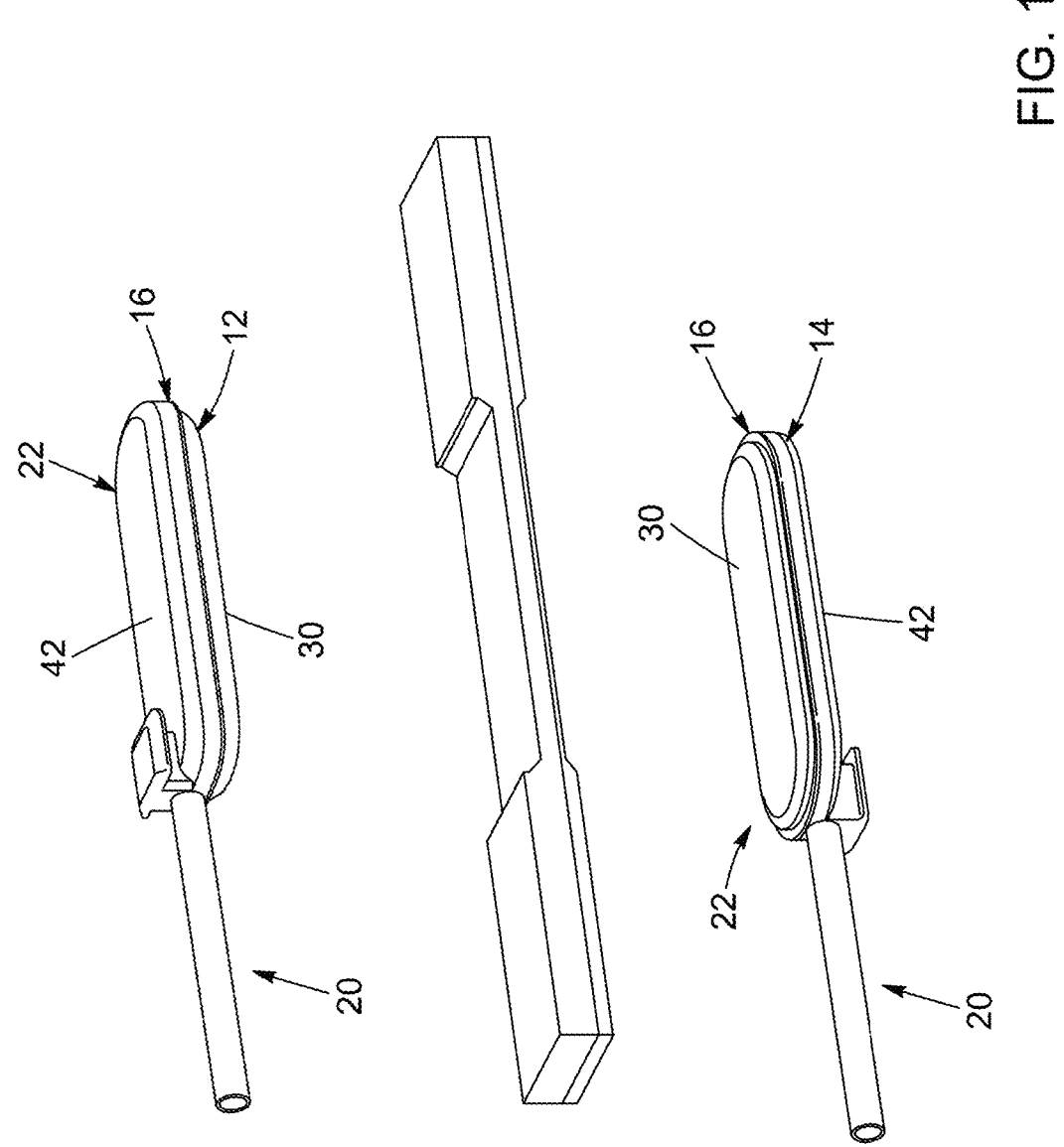
FIG. 1 is an exploded perspective view of a first magnetic implant shown on one side of a desired site of an anastomosis and of a second magnetic implant shown on another side of the desired site of the anastomosis, with a vessel wall of a first hollow organ and a vessel wall of a second hollow organ being shown therebetween, in accordance with an implementation.
Figure 2:
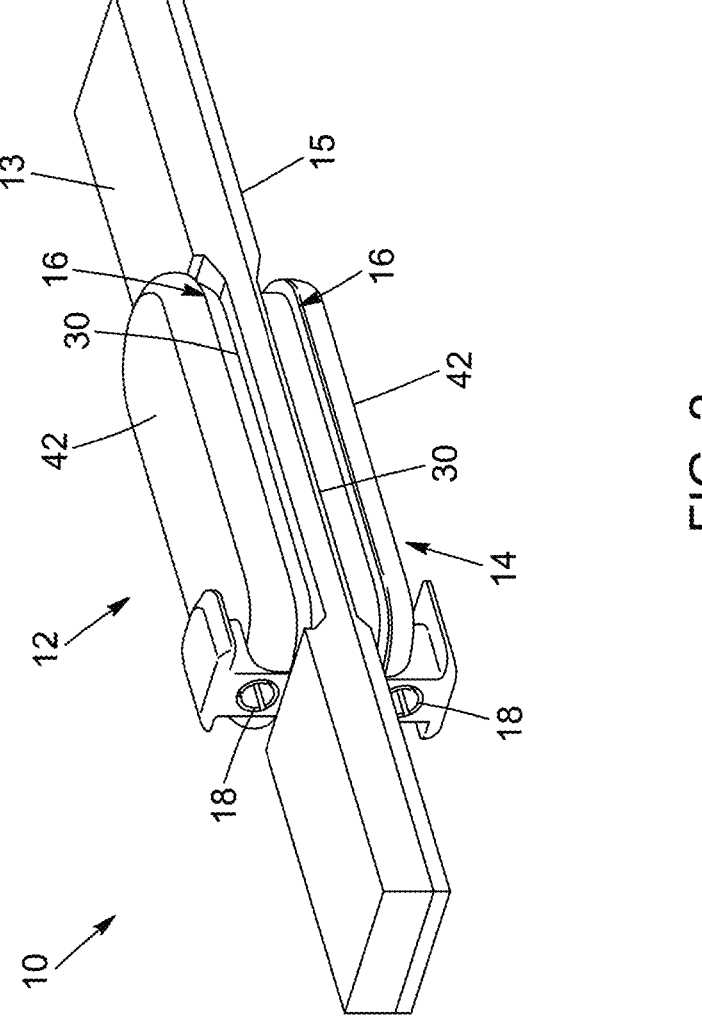
FIG. 2 is a perspective view of the first and second magnetic implants shown in FIG. 1, with the first magnetic implant being shown in contact with the vessel wall of the first hollow organ and the second magnetic implant being shown in contact with the vessel wall of the second hollow organ, at the desired site of the anastomosis.
Figure 3:
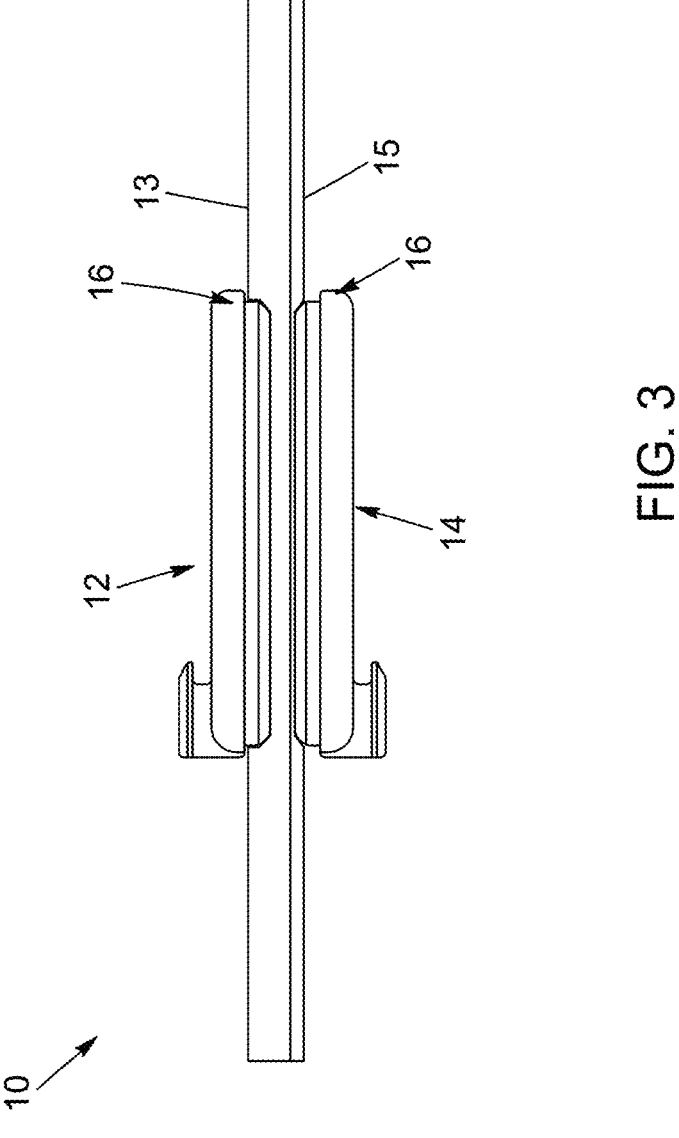
FIG. 3 is a side view of the first and second magnetic implants shown in FIG. 2.
Figure 4A:
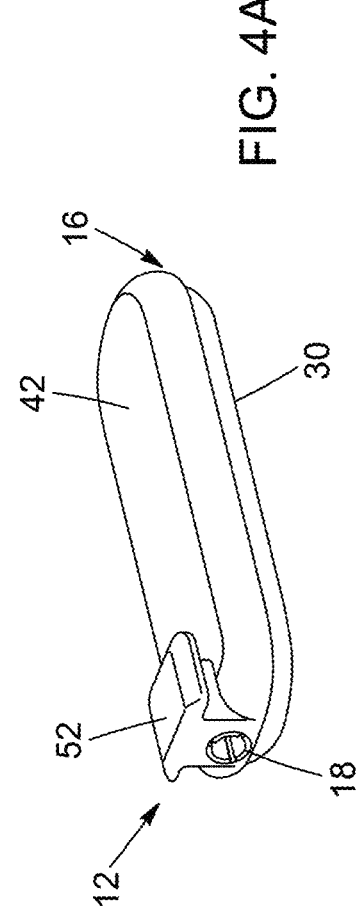
FIG. 4A is a perspective view of a magnetic implant and of a retention member, in accordance with an implementation.
Figure 4B:
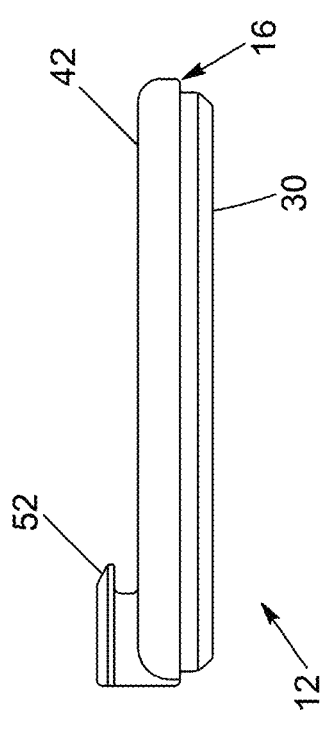
FIG. 4B is a side view of the magnetic implant of FIG. 4A.
Figure 5:
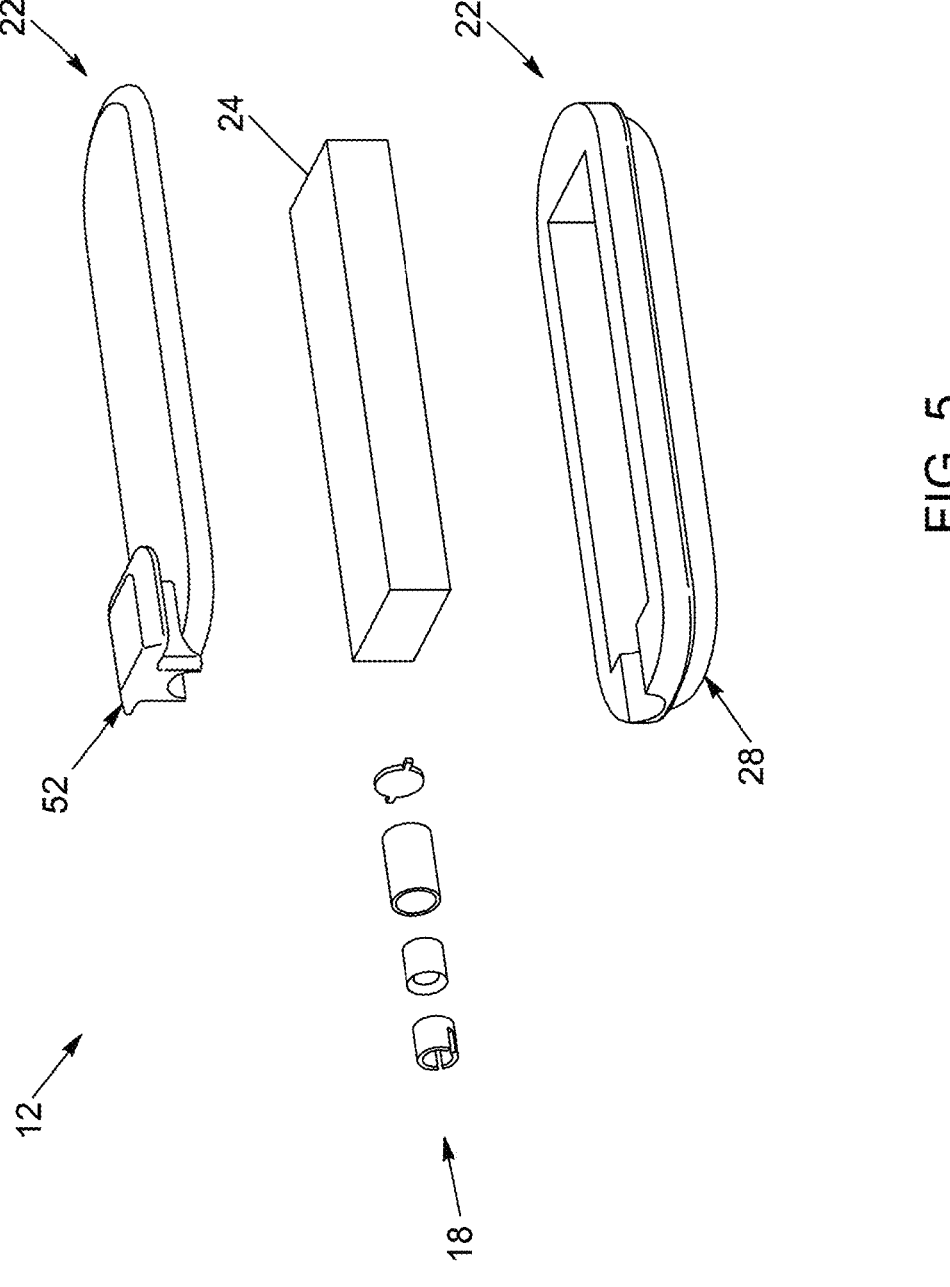
FIG. 5 is an exploded view of the magnetic implant of FIG. 4A.

Techniques described herein relate to systems, devices and methods for assisting in the deployment and coupling of a pair of first and second magnetic implants used for forming a magnetic compression anastomosis between two adjacent walls of hollow organs of the digestive system of a patient, in the context of procedures to treat various medical conditions associated with the digestive system. Such assistance can include the retrieval of a magnetic implant from an unsuitable location within the digestive system. The unsuitable location of the magnetic implant can be the result for instance of an unplanned disengagement of the magnetic implant from its corresponding delivery device, which can be an endoscopic instrument or a laparoscopic instrument, for example. The unsuitable location of the magnetic implant can also be the result of an unsuccessful magnetic coupling of the pair of magnetic implants, which can occur for various reasons.

The retrieval of the magnetic implant from the unsuitable location can be performed using a retrieving device configured to magnetically engage one of the first and second magnetic implants. The retrieving device can include a flexible housing comprising a housing wall defining a retriever magnet receiving cavity. A plurality of retriever magnets can be provided in series within the retriever magnet receiving cavity. The combination of the flexible nature of the housing and the series of retriever magnets received within retriever magnet receiving cavity can contribute to facilitate navigation of the retrieving device within the tortuous path of the digestive tract, while reducing the risks of the retrieving device causing injury or damage to the lining of the digestive tract. The retrieving device can thus be navigated within the digestive tract and modify its configuration to negotiate the curves of the digestive tract. The retrieving device can also include a distal plug that includes atraumatic features, instead of being pointy, which can also contribute to reducing risks of the retrieving device causing injury or damage to the lining of the digestive tract.

The configuration of the retrieving device enables the magnetic engagement with the magnetic implant intended to be retrieved, for instance by simply approaching the retrieving device within a given radius of the magnetic implant so that the retriever magnets of the retrieving device can be magnetically attracted to the magnetic implant, and the retrieving device contacts a main surface of the magnetic implants and thus dock with the magnetic implant, without having to further anchor any other feature of the retrieving device to the magnetic implant, or without having to grab a loop provided on the magnetic implant, for instance.

The flexibility of the flexible housing can be achieved in various ways. In some implementations, the housing wall of the flexible housing can define retriever housing slots extending laterally around a portion of the housing wall. The presence of the retriever housing slots around the housing wall and thus the removal of physical matter at strategic locations around the housing wall can enable the housing wall to bend in response to an applied force.

The retrieving device can be used in a system for retrieving a first magnetic implant of a pair of magnetic implants configured for forming an anastomosis between two adjacent walls of a digestive tract of a patient. In addition to the retrieving device, the system can include a delivery wire engageable with a delivery attachment provided at a proximal end of the flexible housing, and to a handle, such that the delivery wire extends between the retrieving device and the handle for navigating the retrieving device within the digestive device and bring the retrieving device to the location of the magnetic implant to be retrieved. The handle can be manipulated by a healthcare provider to navigate the retrieving device to the location of the magnetic implant to be retrieved.

Once the retrieving device is magnetically engaged with the magnetic implant, the retrieving device can be navigated by the healthcare provider via the delivery wire and handle to modify the location of the magnetic implant. The magnetic attraction between the retrieving device and the magnetic implant can thus be sufficient to maintain the magnetic engagement when the retrieving device is moved by the healthcare provided via the delivery wire and handle. In some implementations, the retrieving device can be used to remove the magnetic implant out of the digestive tract of the patient, and the healthcare provider can subsequently reintroduce the magnetic implant into the digestive tract at the desired site of the anastomosis. In other implementations, the retrieving device can be used to correct the positioning of the magnetic implant from the unsuitable location to the desired site of the anastomosis.

Once both the first and second magnetic implants are positioned on either side of the desired site of the anastomosis, the first and second magnetic implants can be magnetically coupled together to compress the tissue of the adjacent walls therebetween. Compression of the wall tissue between the two magnetic implants results in a necrotic area that corresponds approximately to the surface area of the compression surface of the magnetic implant pair. Over time, the necrotic area becomes surrounded by an edge of scar tissue, or scarred edge. The formation of scar tissue can include collagen fiber deposition, neovascularization, and epithelial regeneration, and represents a dynamic equilibrium involving cells, their milieu, and the extracellular matrix. Cytokines secreted by platelets and inflammatory cells can promote the formation of new blood vessels and collagen synthesis which, in dynamic balance with collagen degradation, can contribute to determine the healing response. Two components of collagen are hydroxyproline and hydroxylysine, with hydroxyproline being synthesized under conditions of oxidative stress via the hydroxylation of proline, and being involved in the cellular transport of collagen. The synthesis and transport of wound collagen can thus be understood by monitoring the hydroxyproline content of the wound. The edge of scar tissue can thus be characterized by the fusion, or mechanical bonding, of the walls of each hollow organ through which the anastomosis is formed that occurs in part via fibrosis mechanisms. The scarred edge can thus form a fluid-tight seal around the anastomosis.

Various implementations and features of the magnetic implants and retrieving device will now be described in greater detail in the following paragraphs.

General Description of the System for Forming an Anastomosis

With reference to FIGS. 1 to 6, a system 10 for forming an anastomosis between two adjacent walls of hollow organs of the digestive tract is shown. Referring more particularly to FIG. 1, in the implementation shown, the system 10 includes a first magnetic implant 12 for implantation at a first location in the digestive tract, for instance in the stomach, and a second magnetic implant 14 for implantation at a second location in the digestive tract, for instance in the jejunum. It is to be understood that the term "implant" as used herein refers to a device that is implanted in the digestive tract for a certain period of time, e.g., during a healing time period, and that it can be used interchangeably with the term "device" or "component" for instance. In this implementation, the stomach represents a first hollow organ of the digestive tract into which the first magnetic implant 12 can be implanted, and the jejunum represents a second hollow organ into which the second magnetic implant 14 can be implanted, so as to compress a portion of the stomach wall 13 and a portion of the jejunum wall 15 therebetween.

Figure 6:
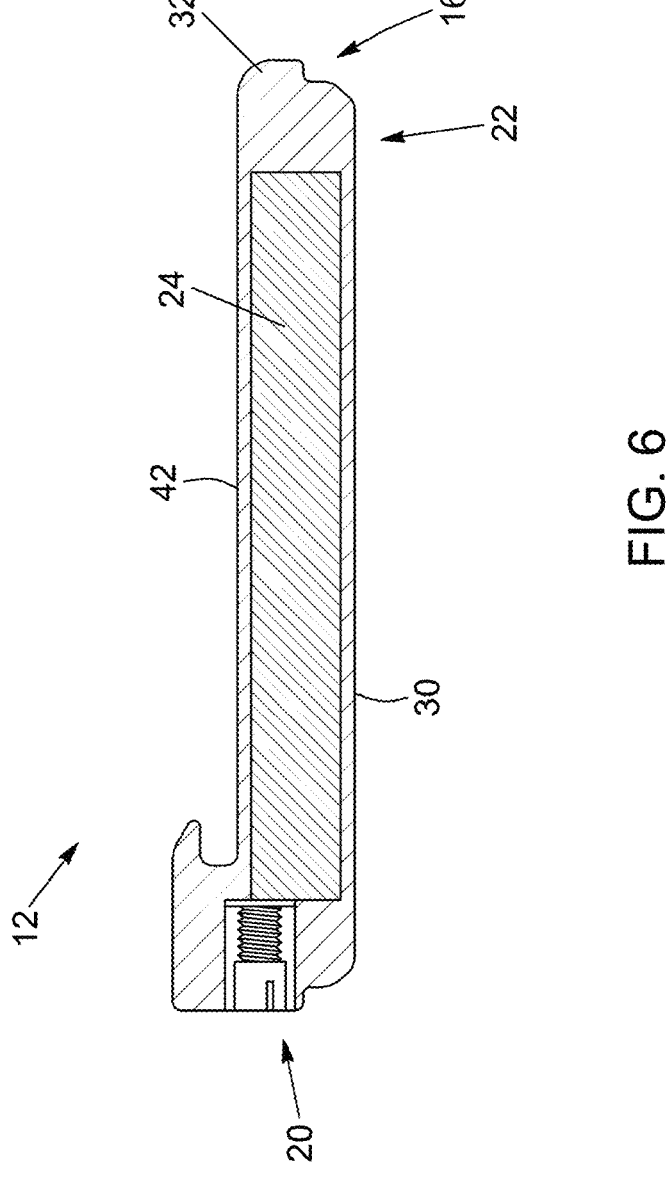
FIG. 6 is a cross-sectional view of the magnetic implant of FIG. 4A.

In the Figures, each one of the first magnetic implant 12 and the second magnetic implant 14 is associated with a retention member 16, which is illustrated as corresponding to a flange 32 in FIG. 6. In the implementation shown, each one of the first magnetic implant 12 and the second magnetic implant 14 also includes a connecting member 18 that can be releasably engageable with a connector 20, which in FIG. 1 is identified as a delivery catheter. In other words, the magnetic implant 12, 14 can include a feature that enables its connection to a connector 20 for navigating the magnetic implant 12, 14 to a desired site for creating the anastomosis. In turn, the connecting member 18 can include any feature that enables a releasable connection of the magnetic implant 12, 14 with the connector 20.

In some implementations and as shown in FIGS. 1 to 6, the magnetic implant 12, 14 can include a housing 22 that encloses a magnet 24 therein. The housing 22 can include for instance an outward portion 26 and an inward portion 28. The inward portion 28 includes the portion of the housing that faces the corresponding other magnetic implant and is involved in the magnetic compression of the tissue, while the outward portion 26 is on the opposed side of the magnetic implant facing away from the tissue being compressed. In this example, the two housing components surround the magnet 24 and can be coupled together around a periphery thereof. Other housing constructions are also possible, where one or more housing components are used to partly or fully enclose the magnet.

Each of these components of the system for forming an anastomosis will now be described in further detail.

Description of the Magnetic Implants

Still referring to FIGS. 1 to 6, the first magnetic implant 12 is a device that is implantable into a first hollow organ of the digestive tract of a patient at a site of a desired anastomosis via the lumen of the first hollow organ. Examples of hollow organs of the digestive tract include the oesophagus, stomach, duodenum, jejunum, ileum, colon, biliary tract, and pancreatic duct. A site of desired anastomosis can be determined according to the condition of the patient, and this aspect will not be discussed further in the context of the present description. As used herein, the expression "magnetic implant" refers to a structure that can be implanted into the chosen hollow organ of the digestive tract, and that can be magnetically attracted to another magnetic implant due to magnetic forces. In some implementations, the magnetic implant can consist of a magnet. In some implementations, the magnetic implant can include a magnet and one or more additional features, such as a housing and/or a connecting member. The two magnetic implants can be substantially the same as each other, or different, in terms of their shape, configuration, construction, and/or material make-up.

The first magnetic implant 12 is used with a second magnetic implant 14 to form an implant pair. The second magnetic implant 14 is a device implantable into a second hollow organ of the digestive tract of the patient to the site of the desired anastomosis via the lumen of the second hollow organ. The second hollow organ of the digestive tract is located in sufficiently close proximity of the first hollow organ to enable the convergence of the respective wall tissue of the first hollow organ and the second hollow organ to eventually form the anastomosis.

The first and second magnetic implants 12, 14 are configured to remain within the digestive tract for at least a given healing time period. The healing time period enables ischemic pressure necrosis of the anastomosis area while providing enough time for the edge of scar tissue to form. In some implementations, after approximately 3 to 5 days following implantation of the pair of magnetic implants at the desired site of the anastomosis, the periphery of the anastomosis is strengthened by collagen deposition, with the formation an edge of scar tissue having an increased tensile strength occurring at an estimated of approximately 7 to 10 days following implantation. The duration for forming the scar tissue can vary depending on the overall health of the individual patient, and depending on the specific parts of the digestive tract being joined. The scar tissue can also gain strength over the course of several additional weeks. In some implementations, it may be desirable for the magnetic implants to be released and passed out of the body of the patient about two weeks after implantation. In some implementations, the healing time period can be about two weeks, or at least two weeks. It is to be understood that the healing time period can be consider to start from the magnetic coupling of the first and second magnetic implants 12, 14 and to end when the first and second magnetic implants 12, 14 are naturally passed out of the patient's body.

Each one of the first and second magnetic implants 12, 14 can have any suitable shape and size determined in accordance with their intended purpose. In some implementations, the size and the shape of the magnetic implant can be determined for instance in accordance with the characteristics of the site of the desired anastomosis, the delivery technique chosen to deliver the magnetic implant to the site of the desired anastomosis, and so on. In some implementations, the magnetic implant can have for example an elliptic shape, a circular shape, an elongated shape, a rectangular shape, an octagonal shape, or any other polygonal shape in terms of its cross-section. The magnetic implant can include rounded corners to facilitate navigation into the digestive tract. The magnetic implant can have an aspect ratio of about 1:1 (e.g., in the case of a circular cross-section) or an aspect ratio of about 1:2 to about 1:40, about 1:3 to about 1:20, about 1:4 to about 1:15, for example, or another aspect ratio. In some implementations, the shape and size of the retention member 16 can be adapted in accordance with the shape and size of the corresponding magnetic implant. For instance, in some implementations, the height of the magnetic implant can be proportional to the thickness of the magnet contained therein and hence desired magnetic strength.

Each of the first and second magnetic implants 12, 14 includes a compression surface 30 that is configured to contact the tissue of the corresponding hollow organ. The compression surface 30 can also be referred to as a tissue-contacting surface, since it is the surface of the magnetic implant that is eventually in contact with the interior wall of the hollow organ once the magnetic implant is delivered to the site of the desired anastomosis. Each of the first and second magnetic implants 12, 14 also includes a lumen-oriented surface 42 opposite the tissue-contacting surface, the lumen-oriented surface 42 generally facing the lumen of the hollow organ once the magnetic implant is delivered to the site of the desired anastomosis. The tissue-contacting surface 30 and the lumen-oriented surface 42 of the magnetic implant can each also be referred to as a main surface of the magnetic implant, in contrast to the surfaces associated with the contour of the magnetic implant.

In some implementations, the compression surface 30 can be substantially continuous and flat, as shown in FIGS. 1 to 6. This can contribute to evenly distribute the force of the magnetic implant onto the tissue once the first and second magnetic implants 12, 14 are magnetically coupled together. In other implementations, the compression surface 30 of the first magnetic implant 12 can have a complementary shape compared to the compression surface 30 of the second magnetic implant 14. For instance, the first magnetic implant 12 can have a curvilinear surface that is inwardly curved, i.e., concave, and the second magnetic implant 14 can have a complimentary curvilinear surface that is outwardly curved, i.e., convex, for the first magnetic implant 12 to mate therewith.

In other implementations, the compression surface 30 can include features such as ridges, crests, furrows, grooves, and the like. For instance, the compression surface 30 of the first magnetic implant 12 can include a series of ridges, and the second magnetic implant 14 can include a complimentary series of furrows such that when the first and second magnetic implants 12, 14 are magnetically coupled, the first and second magnetic implants 12, 14 can interlock and/or self-align to increase the stability of their positioning on their respective sides of the first and second hollow organs.

Figure 7:
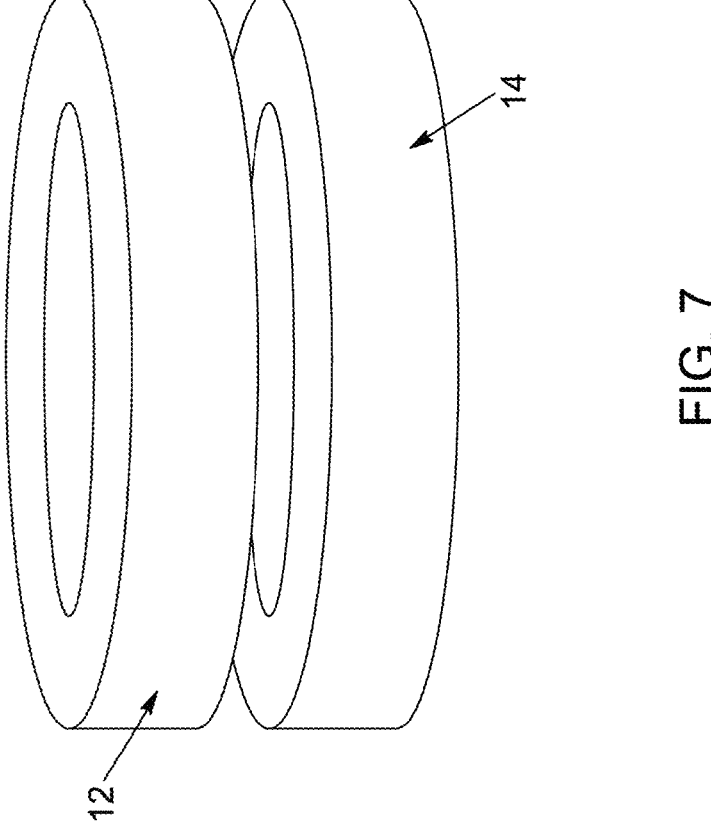
FIG. 7 is a perspective view of first and second magnetic implants having an annular shape, in accordance with an implementation.
Figure 22:
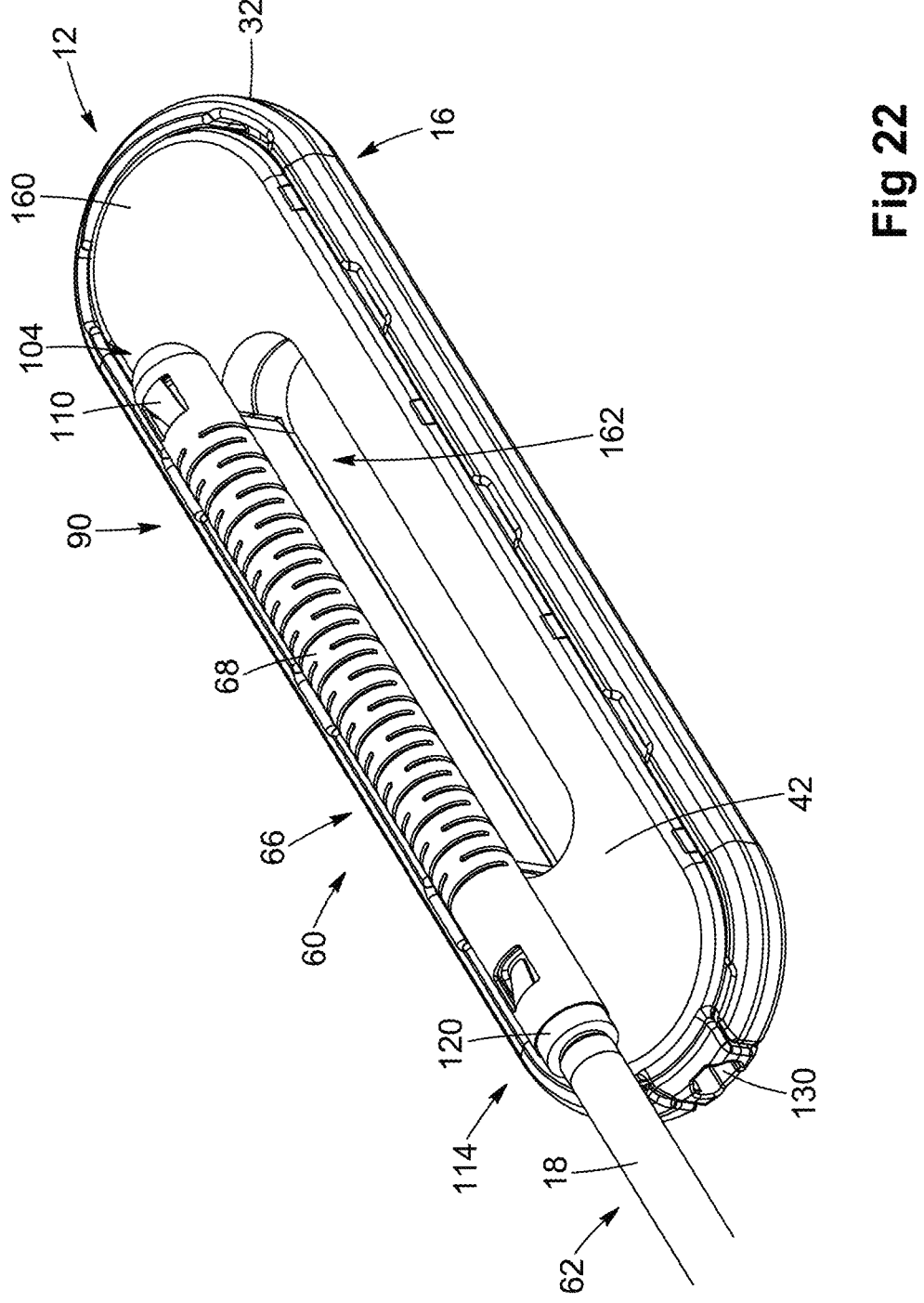
FIG. 22 is a perspective view of a retrieving device, a magnetic implant having a through-hole, and a portion of a delivery wire, in accordance with another implementation.

In yet other implementations, the compression surface 30 can be discontinuous and include void portions, i.e., where the wall tissue is not contacted by a portion of the magnetic implant. For instance, with reference to FIG. 7, the first and second magnetic implants 12, 14 and/or the compression surfaces 30 thereof can have a donut shape, or annular shape. In some implementations, the first and second magnetic implants 12, 14 can have a similar size and a similar or complimentary shape to facilitate the magnetic coupling through the wall tissues of the hollow organs. In other implementations, the first and second magnetic implants can 12, 14 can have a different size and shape depending on the application and the sought-after characteristics of the resulting anastomosis. FIG. 22 illustrates another example of a magnetic implant 12 that includes a discontinuous compression surface because of the presence of a though-hole 162 in a central region of the magnetic body 160 of the magnetic implant 12.

Figure 23:
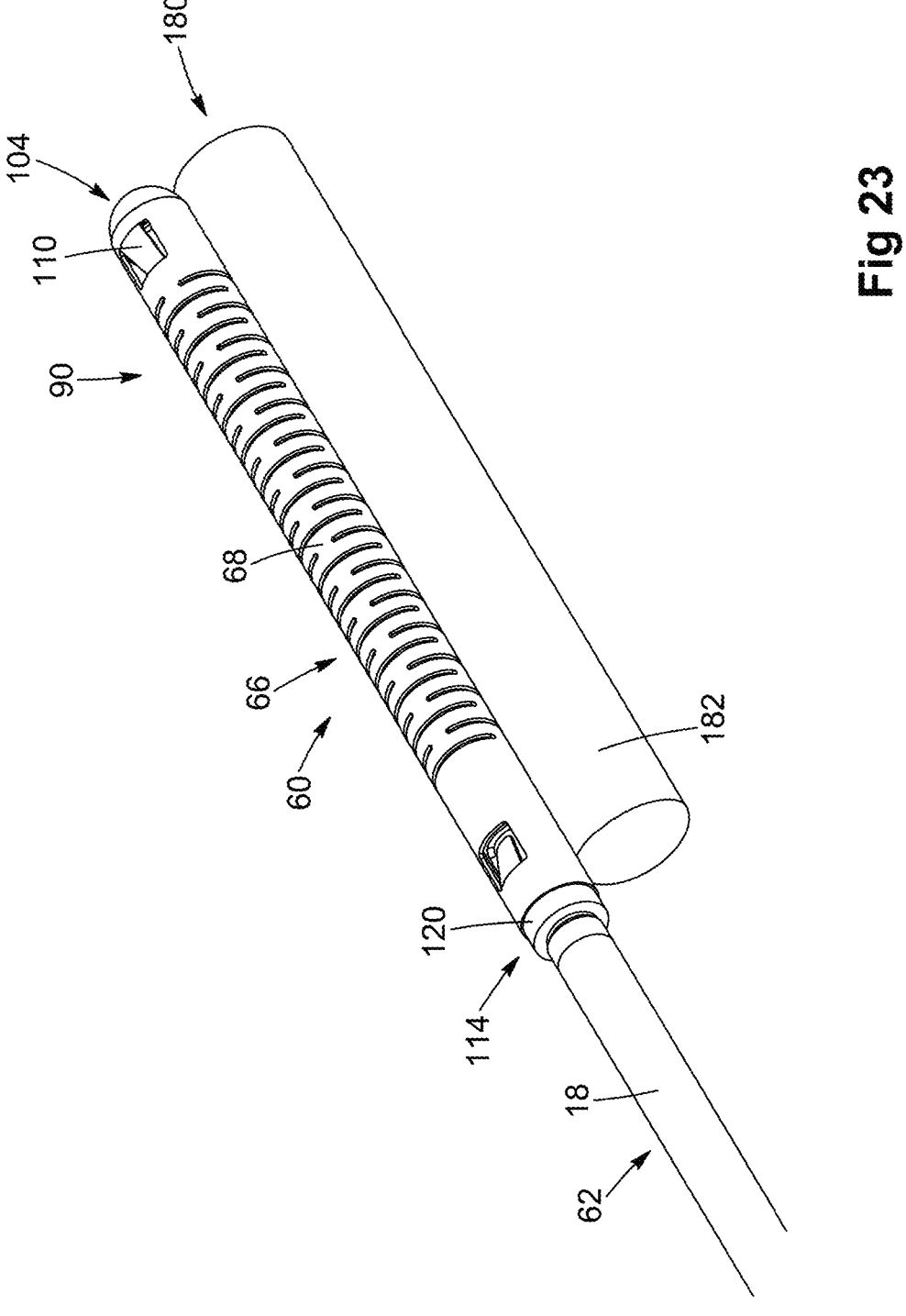
FIG. 23 is a perspective view of a retrieving device, a cylindrical magnetic implant, and a portion of a delivery wire, in accordance with another implementation.

In yet other implementations and as shown in a FIG. 23, the magnetic implant can be a cylindrical magnetic implant.

In some implementations, the magnetic implant 12, 14 can include one or more magnets. The magnet 24 can be any type of suitable magnet composed of the appropriate material. In some implementations, the magnet 24 can be chosen according to its attractive force, i.e., according to the pressure that will be exerted on the surface area of the tissue that will eventually be compressed between the first and second magnetic implants 12, 14. Factors influencing the attractive force of the magnet 24 can include the shape of the magnet 24, the thickness of the magnet 24, the material of which the magnet 24 is made, etc. Example materials include neodymium magnets (e.g., NdFeB magnets), rare earth magnets, and ferrite magnets.

In some implementations, the magnet or magnets of a first magnetic implant may be made of a magnetic material that is not permanently magnetized, such as soft magnetic alloys, e.g., nickel-iron, silicon iron, iron, iron-cobalt, and ferritic stainless steels. In other words, the magnet(s) of respective magnetic implants may not be constructed of two permanent magnets. In other implementations, the magnets of a first and second magnetic implants may be constructed of two permanent magnets.

Housing

In some implementations, the magnetic implant 12, 14 can include a housing 22 configured to house a magnet therein. An example of housing 22 is shown in FIGS. 1 to 6. More particularly in FIGS. 4 and 5, the housing 22 is shown as including an outward portion 26 and an inward portion 28. In the context of the present description, the terms "outward" and "inward" when referring to the housing 22 are used in accordance with a radial reference system, in which the wall of the hollow organ is considered to be outwardly positioned relative to the lumen of the hollow organ. When the housing 22 is present, the outward portion 26 of the housing 22 is the portion that includes the tissue-contacting surface or the compression surface 30 of the magnetic implant, and the inward portion 28 of the housing 22 is the portion that includes the lumen-oriented surface 42. In the implementation shown, the outward portion 26 and the inward portion 28 together fully enclose a single magnet 24 therein. In other implementations, the single magnet can be fully enclosed in a single-piece housing, i.e., a housing 22 that is made of a single unit, the single unit including the tissue-contacting surface 30 and the lumen-oriented surface 42, in accordance with the description above.

In some implementations, the magnetic implant can include a housing that is configured to receive multiple magnets therein. Providing multiple magnets within a single housing can contribute to enhancing the flexibility of the magnetic implant, such that it can become easier to bend when subjected to a force. Alternatively, the multiple magnets can each be received in a corresponding housing, and the multiple magnets can be connected to each other by a cable, a string, a ribbon, a hitch, or a combination thereof, as described above. The description made above regarding the characteristics of the compression surface 30 of the magnetic implant is applicable to the housing 22 when the housing is present or when housings are present.

Description of the Retrieving Device

Figure 8:
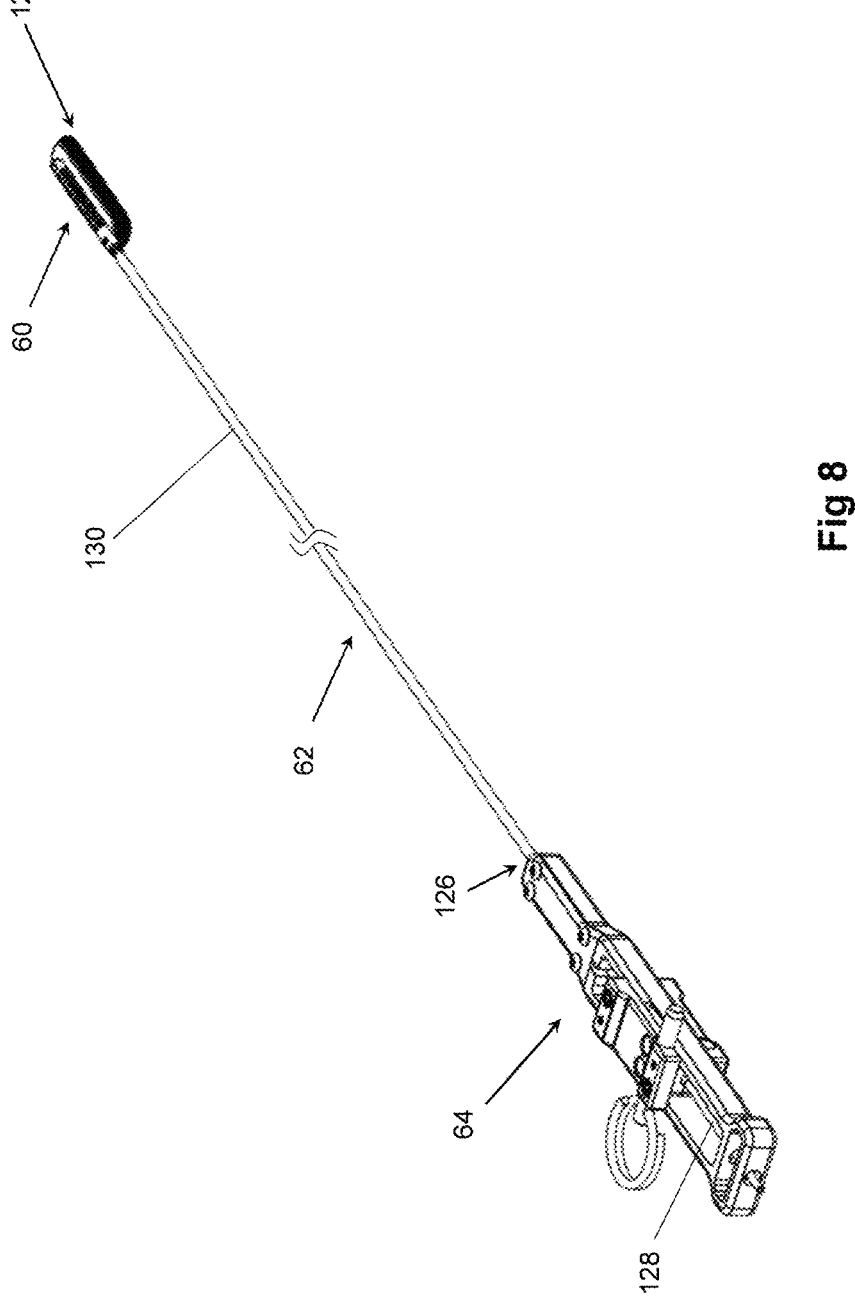
FIG. 8 is a perspective view of a handle, a delivery wire and a retrieving device, the retrieving device being magnetically engaged with a magnetic implant, in accordance with an implementation.
Figure 9:
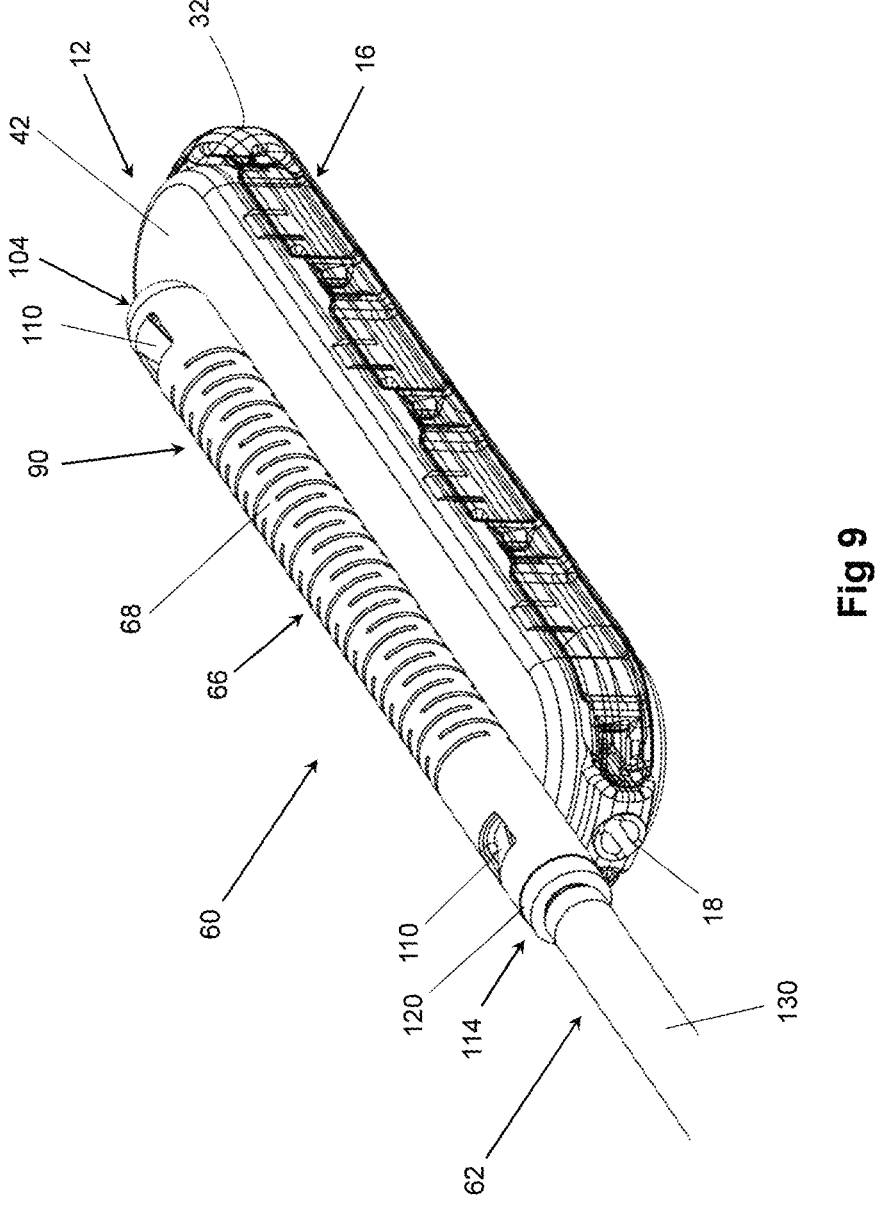
FIG. 9 is an enlarged perspective view of the retrieving device, the magnetic implant, and a portion of the delivery wire shown in FIG. 8.
Figure 24:
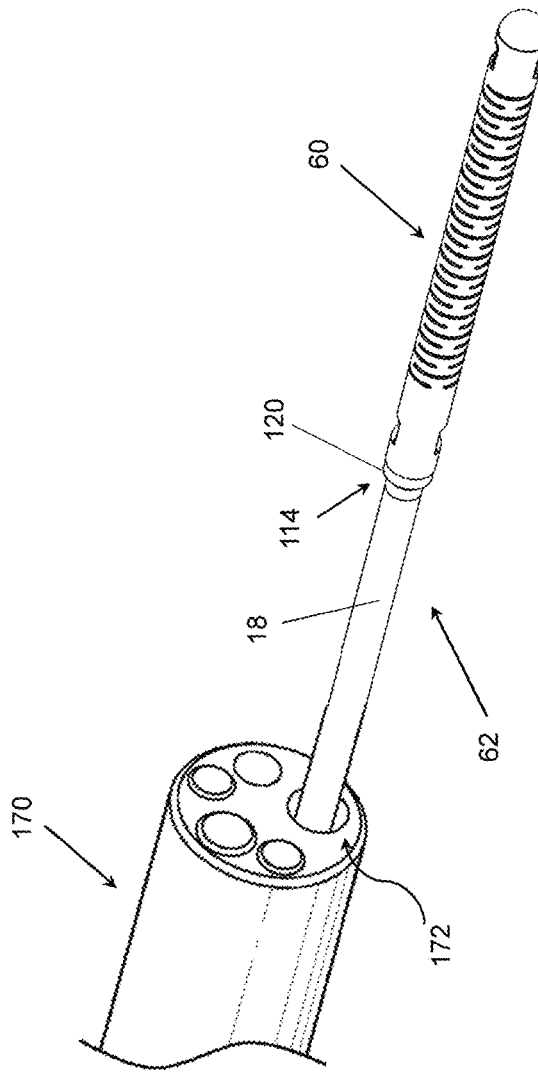
FIG. 24 is a perspective view of a portion of an endoscope, a delivery wire and a retrieving device, in accordance with an implementation.

With reference to FIG. 8, a retrieving device 60 is shown engaged with a delivery wire 62, which in turn is engaged with a handle 64. The retrieving device 60 is further shown magnetically engaged with a magnetic implant of a pair of magnetic implants, which can be for instance the first magnetic implant 12 described above. The delivery wire 62 is flexible to enable navigation of the retrieving device 60 within the digestive tract. In some implementations, the delivery wire 62 is configured for insertion within a working channel of an endoscope. An example of an endoscope 170 having a working channel 172 is shown in FIG. 24, with the delivery wire 62 being inserted into the working channel 172 of the endoscope 170. The endoscope can be any type of suitable endoscope such as a gastroscope, a colonoscope, a duodenoscope, a bronchoscope, a cystoscope, or a ureteroscope, for instance.

Figure 25:
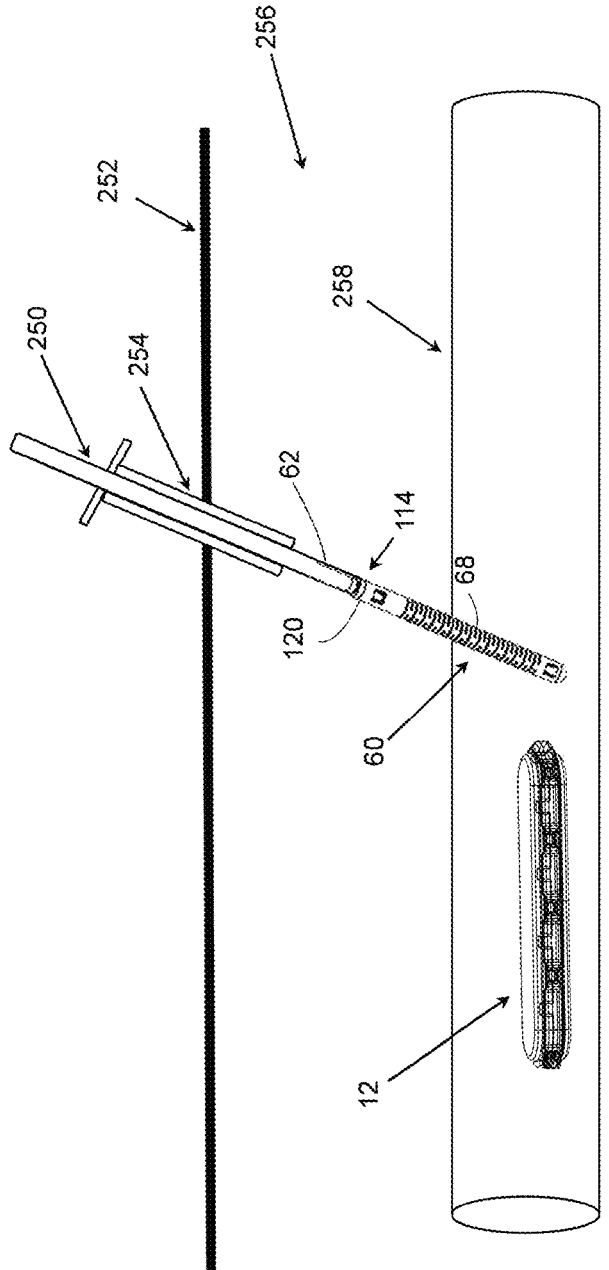
FIG. 25 is a perspective view of a laparoscopic instrument inserted into a trocar, a delivery wire, a retrieving device and a magnetic implant, in accordance with an implementation.

The handle 64 can be any type of handle that can be manipulated by a healthcare provider and that can interact with the delivery wire 62 to modify the length of the delivery wire 62 introduced into the digestive tract. In some implementations, the delivery wire 62 can be configured similarly as a delivery catheter typically used in cooperation with an endoscope. In FIG. 25, the retrieving device 60 is shown as being coupled to a laparoscopic instrument 250. The laparoscopic instrument 250 is configured to be introduced into the abdominal cavity 256 of the patient. In the implementation shown, the laparoscopic instrument 250 is inserted into the abdominal cavity 256 of the patient via a trocar 254 that is placed through the abdominal wall 252, and then the retrieving device 60 is inserted into the digestive system, exemplified as the duodenum 258 in FIG. 25. Alternatively, the laparoscopic trocar can be a percutaneous trocar. The laparoscopic trocar and the percutaneous trocar can be in the context of an enterotomy, a gastrotomy, a colotomy, or a cholecystostomy, for instance. The incision can also be made to access the bile duct.

With reference to FIGS. 9 to 11, 22 and 23, an enlarged view of the retrieving device 60, the delivery wire 62 and the first magnetic implant 12 of FIG. 8 is shown. As mentioned above, the first magnetic implant 12 includes a retention member 16 exemplified as a flange 32, a connecting member 18, and a lumen-oriented surface 42, which can also be referred to as a main surface of the magnetic implant 12. It is to be understood that when referring to a "first" magnetic implant that is magnetically engaged with the retrieving device 60, this reference can also interchangeably be made to a "second" magnetic implant, depending on the magnetic implant that needs to be retrieved. In addition, the main surface of the magnetic implant can either be the lumen-oriented surface 42 or the tissue-contacting surface 30, depending on the position and orientation of the magnetic implant 12 when the retrieving device 60 "catches" the magnetic implant. In other words, the magnetic implant 12 can be oriented randomly when at the unsuitable location in the digestive tract, and as such the retrieving device 60 can magnetically engage any of the main surfaces of the magnetic implant irrespective of the positioning of the magnetic implant. In other implementations, the retrieving device 60 can magnetically engage a peripheral surface of the magnetic implant, i.e., a surface extending between the compression surface 30 and the lumen-oriented surface 42, along the contour of the magnetic implant.

In FIG. 22, the magnetic implant 12 includes comprising a magnetic body 160 having a lumen-oriented surface 42 and a tissue-contacting surface located opposite the lumen-oriented surface 42 (not shown), the magnetic body 160 defining a through-hole 162 extending between the tissue-contacting surface and the lumen-oriented surface 42. In such implementations, the main surfaces of the magnetic implant 12 remain the tissue-contacting surface and the lumen-oriented surface, such that the retrieving device 60 can magnetically engage any of the main surfaces of the magnetic implant irrespective of the positioning of the magnetic implant. The magnetic attraction between the magnetic implant 12 and the retrieving device 60 will occur between the magnetic body 160 of the magnetic implant 12 and the retrieving device 60. Further details regarding possible configurations of a magnetic implant with a through-hole are described in PCT application No. PCT/US2024/034799, which is incorporated herein by reference in its entirety.

In FIG. 23, the magnetic implant 12 is exemplified as a cylindrical magnetic implant 180 that includes a tissue-contacting surface 182 as a main surface. The retriever device 60 can thus dock onto the cylindrical magnetic implant 180 at any location of the circumferential outer surface of the cylindrical magnetic implant 180. Such a cylindrical magnetic implant can be used in the context of an anastomosis involving the biliary tract, the pancreatic canal or the hepatic canal, for instance. Further details regarding possible configurations of a cylindrical magnetic implant are described in PCT application No. PCT/US2024/048518, which is incorporated herein by reference in its entirety.

Referring to FIGS. 9 to 20, the retrieving device 60 includes a flexible housing 66 comprising a housing wall 68 defining a retriever magnet receiving cavity 70. In the implementation shown, the flexible housing 66 is exemplified as being tubular, with a circular cross-section. It is to be understood that in other implementations, the shape of the flexible housing 66 can be other than tubular. For instance, the flexible housing can be a rectangular prism. Alternatively, the cross-section of the flexible housing can take any suitable polygonal shape. In some implementations, the housing wall 68 of the flexible housing includes side walls that have substantially identical shapes and dimensions, such as a rectangular prism, a pentagonal prism, an hexagonal prism, an octagonal prism and so on, so that any side of the flexible housing 66 of the retrieving device 60 can magnetically engage the main surface of the magnetic implant, irrespective of the orientation of the retrieving device 60 when in proximity of the magnetic implant. In other implementations, for instance if a specific orientation of the retrieving device 60 is desired when the magnetic engagement with the main surface of the magnetic implant occurs, the housing wall 68 of the flexible housing 60 can include side walls having different shapes and dimensions such that a given face of the flexible housing 66 preferentially contacts the main surface of the magnetic implant.

Retriever Magnets

Referring to FIGS. 9 to 20, the retriever magnet receiving cavity 70 is configured to receive a plurality of retriever magnets 72 therein. In the implementation shown in FIGS. 12 to 14, 18 and 20, five retriever magnets 72 are received within the retriever magnet receiving cavity 70. The retriever magnets 72 are configured to be placed adjacent to each other, in series, i.e., in an end-to-end fashion, within the retriever magnet receiving cavity 70, such that once the retriever magnets 72 are within retriever magnet receiving cavity 70, a magnetic portion 74 of the retrieving device 60 can be obtained.

Figure 12:
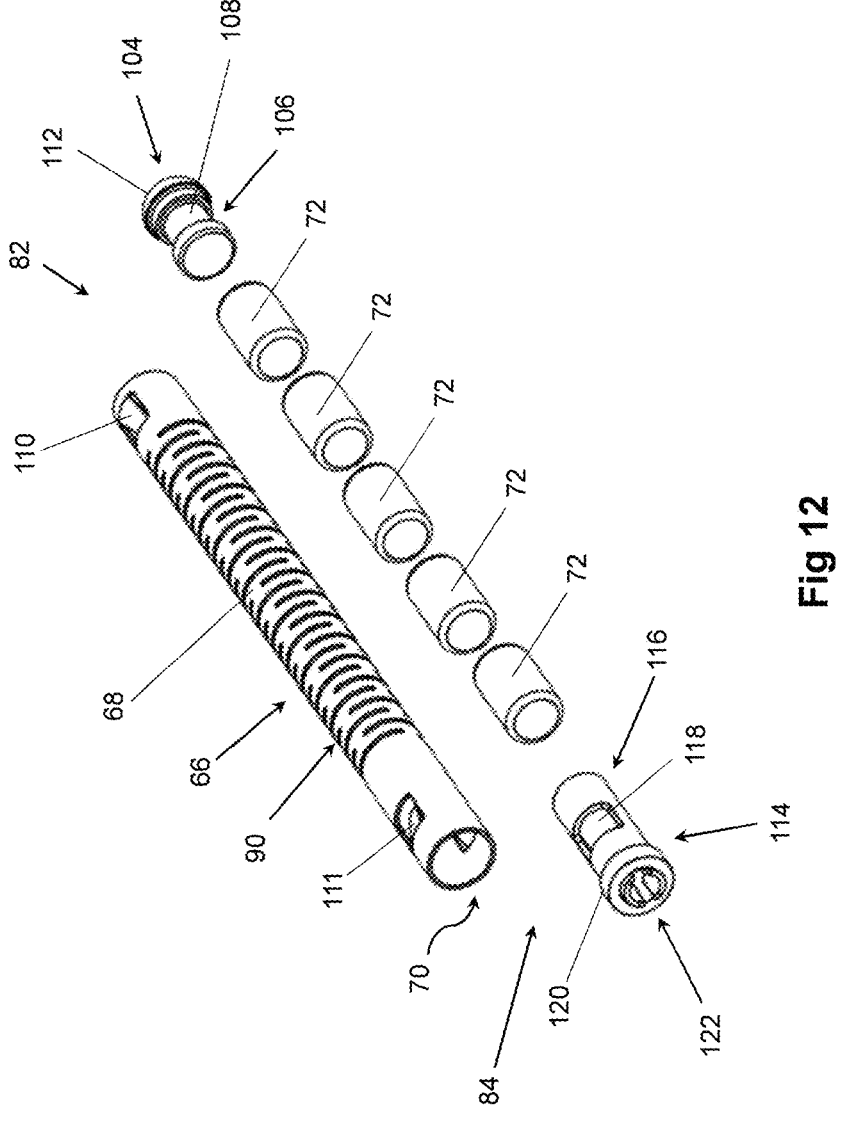
FIG. 12 is an exploded perspective view of the retrieving device of FIG. 8, showing a plurality of retriever magnets, a proximal stopper, a distal plug and a flexible housing.
Figure 13:
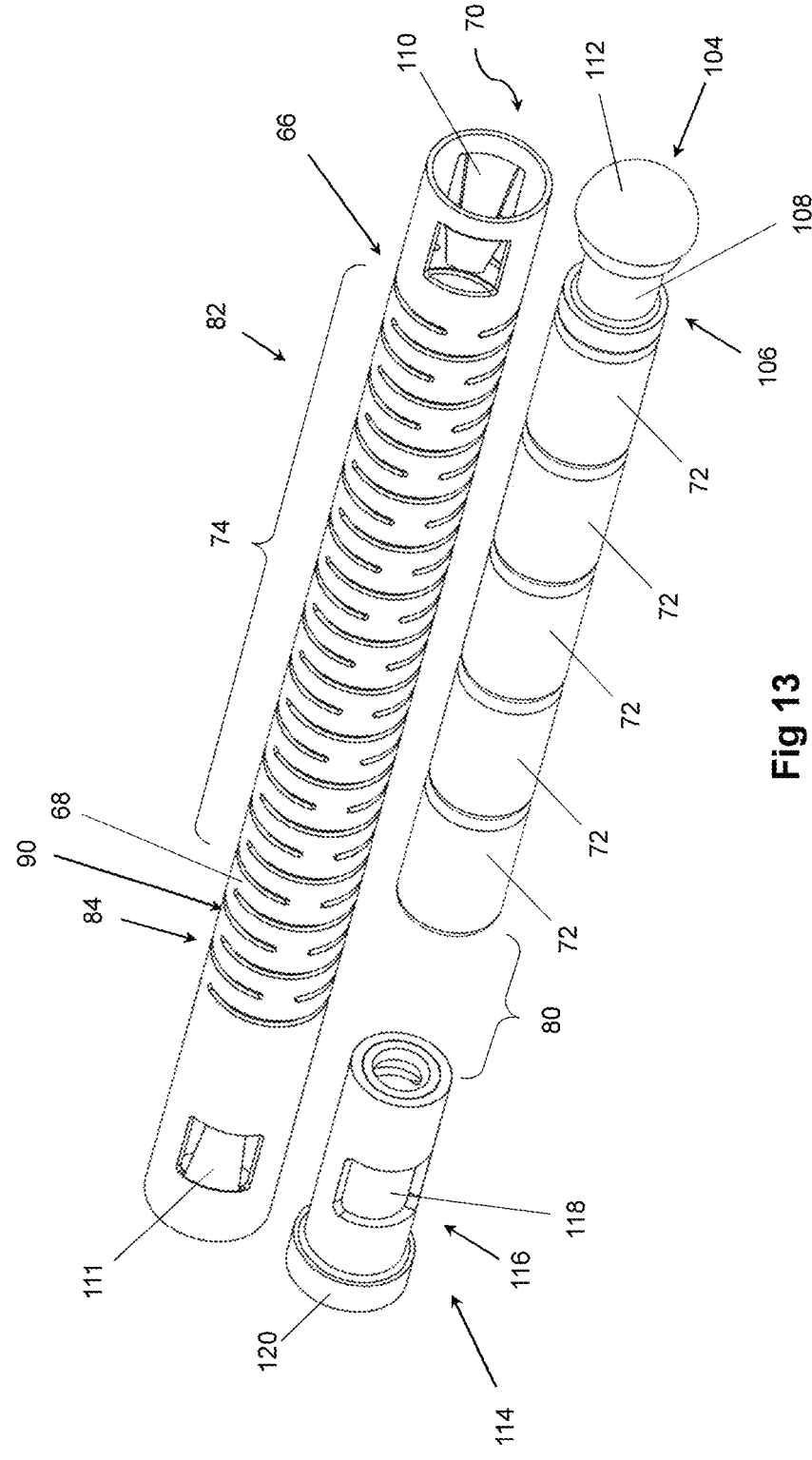
FIG. 13 is an exploded perspective view of the retrieving device of FIG. 8, showing the plurality of retriever magnets, the proximal stopper, the distal plug and the flexible housing.
Figure 14:
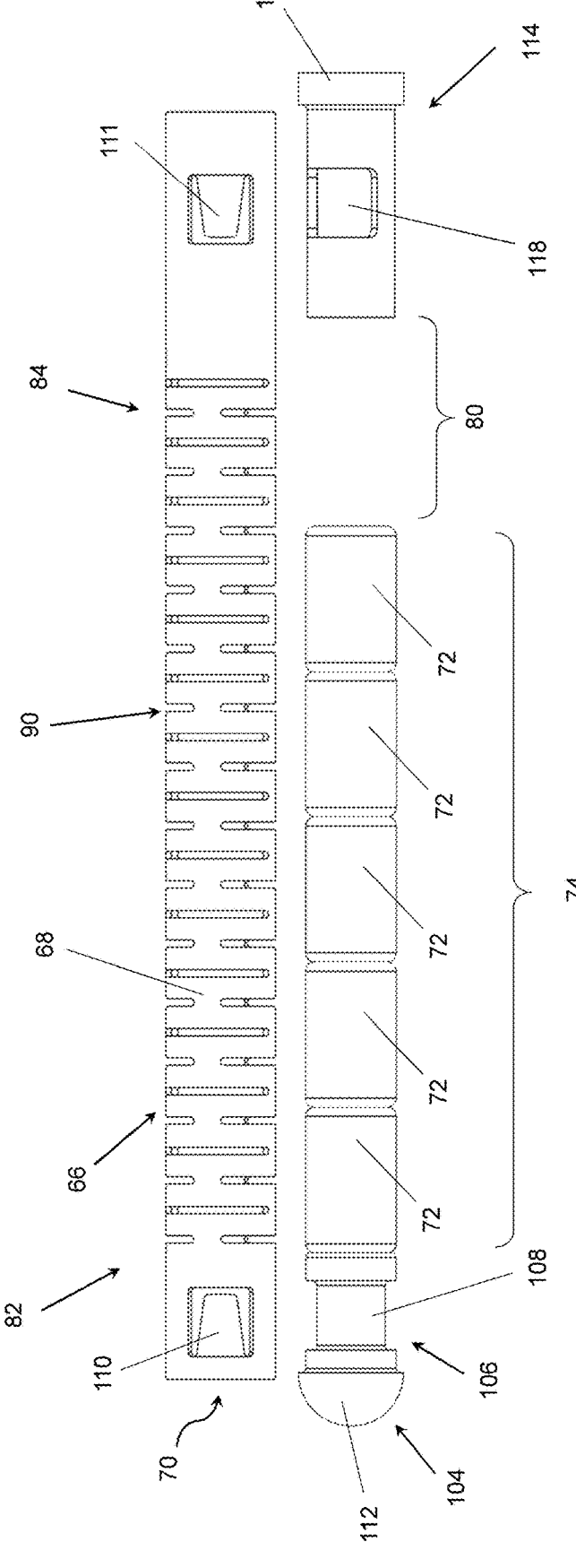
FIG. 14 is an exploded side view of the retrieving device of FIG. 8, showing the plurality of retriever magnets, the proximal stopper, the distal plug and the flexible housing.

FIGS. 12 to 14 show the retriever magnets 72 outside of the flexible housing 66, for illustrative purposes. With reference more particularly to FIGS. 12 and 13, the magnetic portion 74 of the retrieving device 60 is shown in a distal region 82 of the retrieving device 60. When the retriever magnets 72 are concentrated in the distal region 82 of the retrieving device 60, a non-magnetic portion 80 of the retrieving device 60 is thus created in a proximal region 84 of the retrieving device 60. It is to be understood that given that the retriever magnets 72 can freely move within the retriever magnet receiving cavity 70, the localization of the magnetic portion 74 and the non-magnetic portion 80 can vary. For instance, if the retriever magnets 72 are momentarily spaced-apart from each other, which can occur for example when the flexible housing 66 is bent, the non-magnetic portion 80 can include the space defined between adjacent ones of the retriever magnets 72, instead of being localized either at the distal region 82 or the proximal region 84 of the retrieving device 60. In addition, although the retriever magnets 72 are shown in the distal region 82 of the retrieving device 60 thus defining the magnetic portion 74 in the distal region 82 of the retrieving device 60 as well, it is to be understood that the retriever magnets 72 can also be located in the proximal region 84 of the retrieving device 60 thus defining the magnetic portion 74 in the proximal region 84 of the retrieving device 60 as well. Given that the retriever magnets 72 can move freely within the retriever magnet receiving cavity 70, a given number of retriever magnets 72 can be located in the proximal region 84 of the retrieving device 60, while another number of retriever magnets 72 can be located in the distal region 82 of the retrieving device 60, such that a non-magnetic portion 80 of the retrieving device 60 can be located in a central region of the retrieving device 60. In some implementations, this configuration can contribute to facilitate bending of the flexible housing 66 of the retrieving device 60.

Although in FIGS. 12 to 14, five retriever magnets 72 are shown, it is to be understood that any number of retriever magnets 72 can be present. When more than one retriever magnet 72 is present, this can contribute to provide enhanced flexibility to the retrieving device 60. For instance, if two retriever magnets 72 are present, one can be located in the distal region 82 of the retrieving device 60 and another one can be located in the proximal region 84 of the retrieving device 60, such that bending of the retrieving device 60 in a central region thereof can be facilitated. Generally speaking, it can be expected that a higher number of retriever magnets 72 can increase the resulting flexibility of the retriever device 60. Alternatively, there can be a single retriever magnet 72 received within the flexible housing 66. In some implementations, a single retriever magnet 72 received within the flexible housing 66 can contribute to facilitate self-alignment of the retrieving device 60 with the magnetic implant to retrieve.

Figure 34:
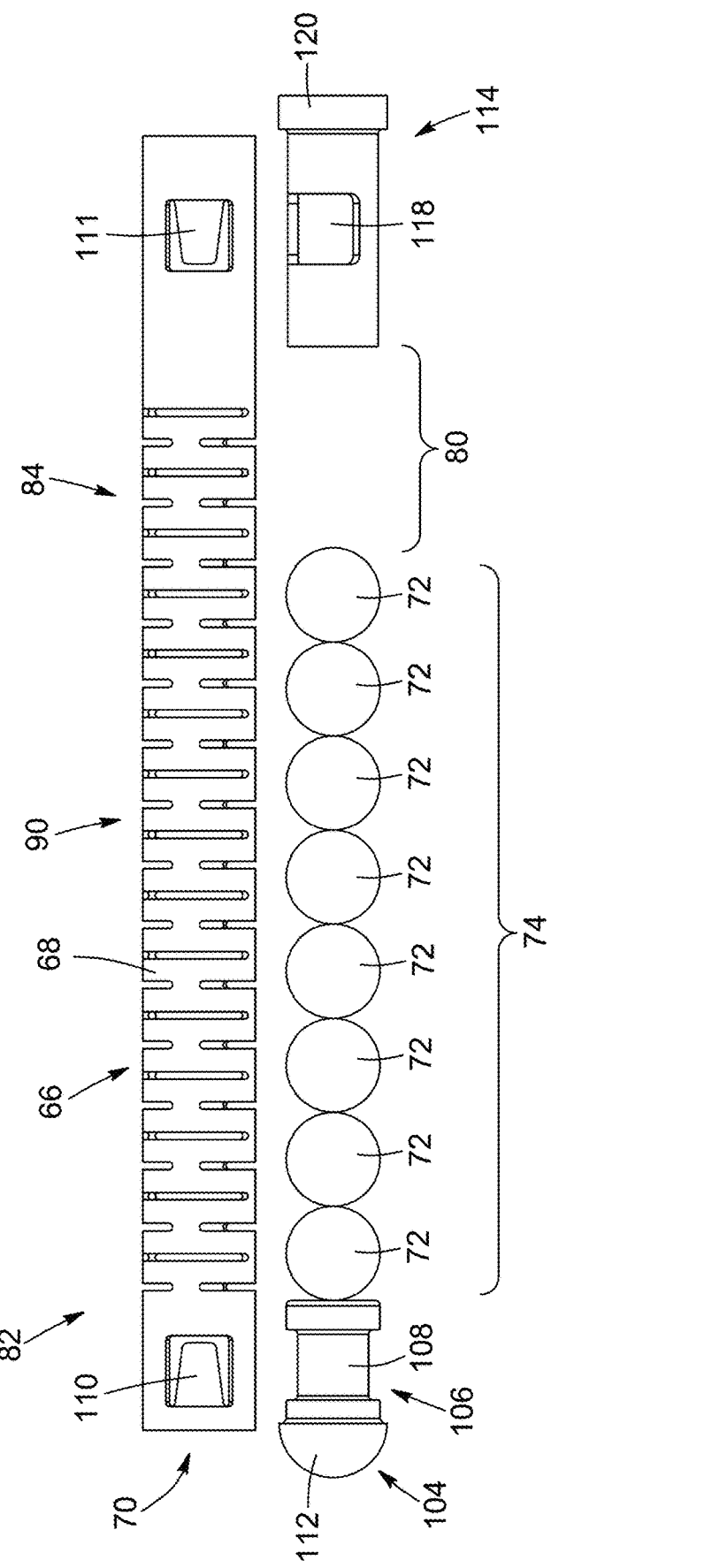
FIG. 34 is an exploded side view of a retrieving device in accordance with another implementation, showing a plurality of retriever magnets, a proximal stopper, a distal plug and a flexible housing including retriever housing slots, the retriever magnets being shaped as substantially spherical beads.

The retriever magnets 72 each have a cross-section that is complimentary to the cross-section of the flexible housing 66. In other words, when the flexible housing 66 is tubular, the retriever magnets 72 can have a circular cross-section. With such a configuration, the retriever magnets 72 can rotate freely within the retriever magnet receiving cavity 70, which can contribute to facilitate their displacement, including their translational displacement in a longitudinal direction, within the retriever magnet receiving cavity 70 when the flexible housing 66 is subjected to bending. In implementations where the flexible housing 66 has a polygonal cross-section, the retriever magnets 72 can either have a circular cross-section or a complimentary polygonal cross-section. When the flexible housing 66 has a polygonal cross-section and the retriever magnets 72 have a circular cross-section, the circular cross-section can be sufficiently small relative to the diameter of the retriever magnet receiving cavity 70, such that the retriever magnets 72 can rotate freely within the retriever magnet receiving cavity 70 and can be subjected to a translational displacement in a longitudinal direction. When the flexible housing 66 has a polygonal cross-section and the retriever magnets 72 have a complimentary polygonal cross-section, the complimentary polygonal cross-section of the retriever magnets 72 can contribute to interlock the cross-section of the retriever magnets 72 within the retriever magnet receiving cavity 70, thus restricting the displacement of the retriever magnets 72 to a translational displacement in a longitudinal direction. When the retriever magnets 72 have a circular cross-section, it is to be understood that the retriever magnets 72 can have a cylindrical shape such as shown in FIGS. 12 to 14, or the retriever magnets 72 can have a circular cross-section and take the form of substantially spherical beads, for instance, as shown in FIG. 34. When the retriever magnets 72 are shaped like substantially spherical beads (or similar to bearings), it can further contribute to their ease of displacement according to various degrees of freedom within the retriever magnet receiving cavity 70, thus increasing their range of motion within the retriever magnet receiving cavity 70.

Figures 15, 16:
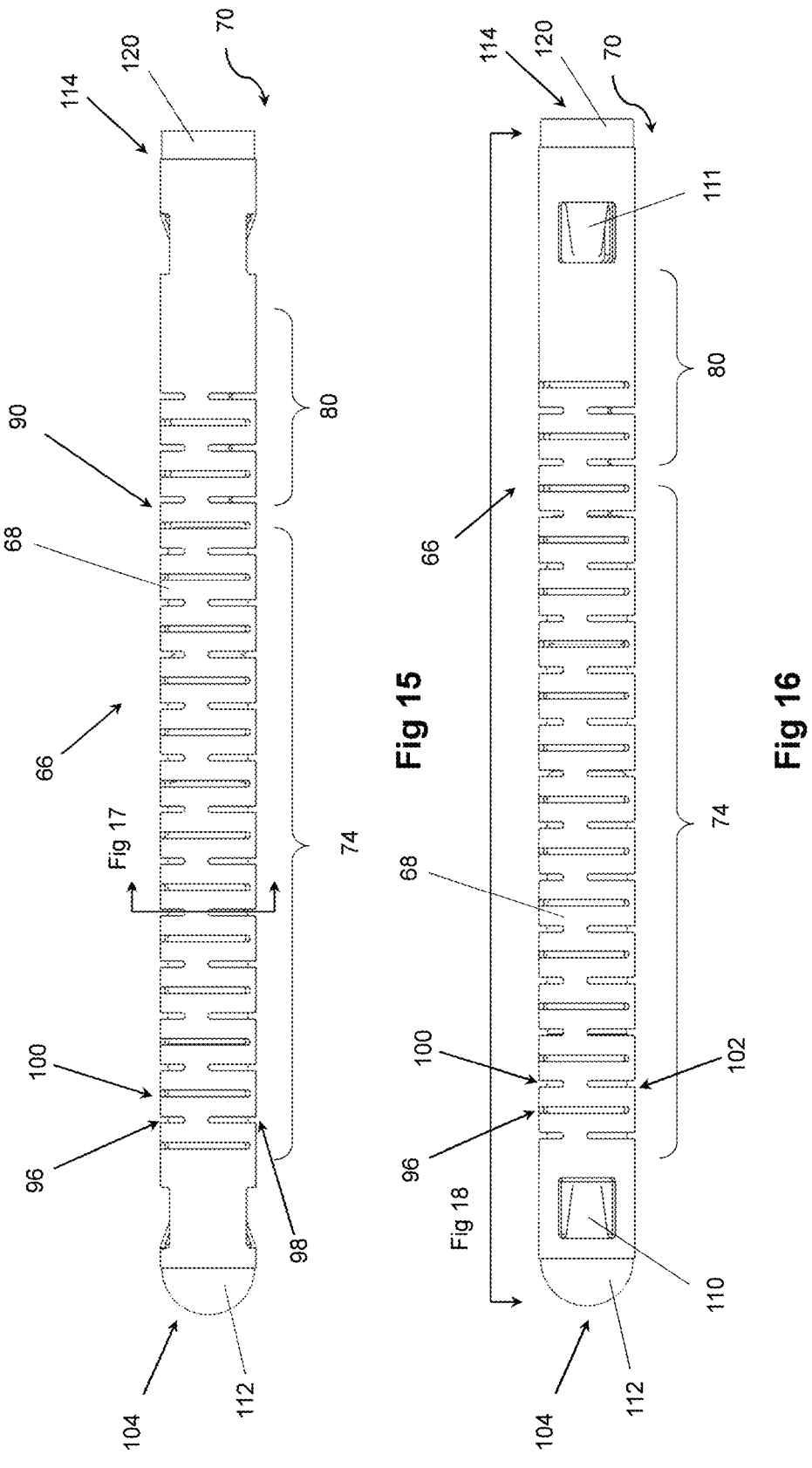
FIG. 15 is a side view of the retrieving device of FIG. 8, showing a magnetic portion and a non-magnetic portion, with retrieving magnets received within a retriever magnet receiving cavity of a flexible housing, a proximal stopper and a distal plug.
FIG. 16 is a side view of the retrieving device of FIG. 15, rotated 90°.
Figures 17, 18:
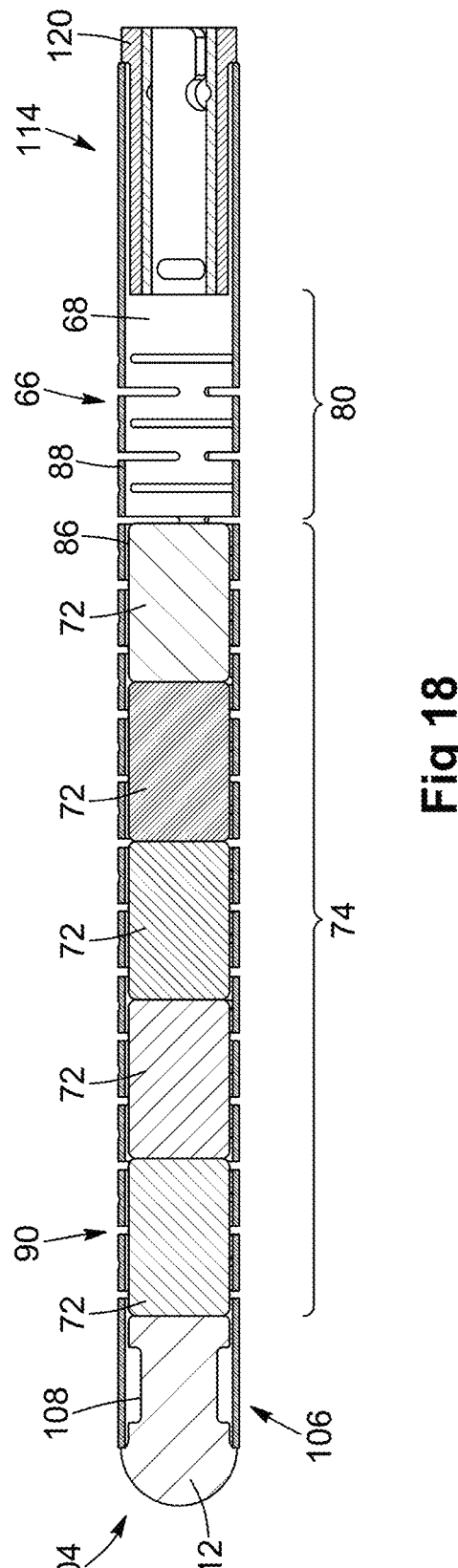
FIG. 17 is a transversal cross-sectional view of the retrieving device of FIG. 15, taken along the "FIG. 17" axis.
FIG. 18 is a longitudinal cross-sectional view of the retrieving device of FIG. 16, taken along the "FIG. 18" axis.

FIG. 17 is a cross-sectional view of the retriever device 60 shown in FIG. 15, with the cross-section taken along a transversal axis of the retriever device 60. FIG. 18 is a cross-sectional view of the retriever device 60 shown in FIG. 16, with the cross-section taken along a longitudinal axis of the retriever device 60, the retriever magnets 72 within the flexible housing 66 being shown adjacent to each other in the retriever magnet receiving cavity 70, the combination of the retriever magnets 72 forming the magnetic portion 74 of the flexible housing 66. In the implementation shown in FIGS. 17 and 18, each of the retriever magnets 72 has a cross-section that is complimentary to the cross-section of the flexible housing 66. The diameter of the retriever magnets 72 is chosen so as to define a displacement void 78 between an outer surface 86 of the retriever magnets 72 and an inner surface 88 of the housing wall 68 of the flexible housing 66. This displacement void 78 between the outer surface 86 of the retriever magnets 72 and the inner surface 88 of the housing wall 68 of the flexible housing 66 can facilitate the movement of the retriever magnets 72 within the retriever magnet receiving cavity 70 when the flexible housing 66 is bent, or flexed. The displacement void 78 can thus enable a certain range of motion of the retriever magnets 72 within the retriever magnet receiving cavity 70. In addition, and as shown in FIG. 14, the overall length of the combination of retriever magnets 72 can be chosen such that is it is smaller than the length of the retriever magnet receiving cavity 70, which can also facilitate displacement of the retriever magnets 72 within the retriever magnet receiving cavity 70, including the translational displacement of the retriever magnets 72 along the longitudinal axis, for instance when the flexible housing 66 is bent or flexed. A balance can be found between the length of the magnetic portion 74 and the length of the non-magnetic portion 80 to facilitate this displacement while providing sufficient magnetic attraction to the retrieving device 60 to magnetically engage with the magnetic implant to retrieve. In some implementations, the length ratio between the length of the magnetic portion 74 and the length of the non-magnetic portion 80 can be between about 10:1 to about 2:1, for instance. In the illustrated implementation, the length ratio between the magnetic portion 74 and the length of the non-magnetic portion 80 is exemplified as being about 4:1.

The retriever magnets of the plurality of retriever magnets 72 together have a magnetic strength that is selected such that a magnetic attraction between the retrieving device 60 and the magnetic implant with which the retrieving device 60 is magnetically engaged can enable the displacement of the magnetic implant along the digestive tract of the patient.

In some implementations, one or more retriever magnets of the plurality of retriever magnets 72 can be made of a magnetic material that is not permanently magnetized, such as soft magnetic alloys, e.g., nickel-iron, silicon iron, iron, iron-cobalt, and ferritic stainless steels. In some implementations, one or more retriever magnets of the plurality of retriever magnets 72 can be constructed of a permanent magnet.

When used in cooperation with magnetic implants that are elongated, the flexible housing 66 of the retrieving device 60 can also be elongated, thus resulting in an elongated flexible housing. Providing an elongated flexible housing can enable having a longer magnetic portion 74 along the flexible housing 66. In turn, the elongated flexible housing with the longer magnetic portion 74 can enable interacting with an elongated magnetic implant and can be beneficial to lengthen the distance along which the contact between the magnetic implant and the retrieving device 60 occurs, which in turn can contribute to enhance the strength of the magnetic interaction between the magnetic implant and the retrieving device 60. With an increased strength of the magnetic interaction between the magnetic implant and the retrieving device 60, there can be a higher probability that the magnetic implant and the retrieving device 60 will remain docketed to each other even if movement is imparted on the retrieving device 60 by the healthcare provider via the delivery device and the handle. On the other hand, it can also be important to take into consideration the length of the flexible housing 66 of the retrieving device 60 and the strength of the retriever magnets 72 received in the retriever magnet receiving cavity 70, such that if an undocking of the retrieving device 70 from the magnetic implant is desired within the digestive tract, it is possible to do so. In the implementation shown in FIGS. 9 to 20, the length of the flexible housing 66 of the retrieving device 60 extends over a majority of the length of the magnetic implant. It is to be understood that the length of the flexible housing 66 can also be smaller than in the illustrated implementation, and can extend for instance over less than a majority of the length of the magnetic implant.

Flexible Housing

The flexibility of the flexible housing 66 can be achieved in various ways. In the implementation shown in FIGS. 9 to 20, the housing wall 68 of the flexible housing 66 defines retriever housing slots 90 extending laterally (i.e., transversally) around a portion of the housing wall 68. The retriever housing slots 90 extend at regular intervals from each other in a predetermined pattern that contributes to providing flexibility to the retriever housing 66. In the implementation shown, given that the flexible housing 66 is tubular, the retriever housing slots 90 extend circumferentially around the portion of the housing wall 66.

Figures 10, 11:
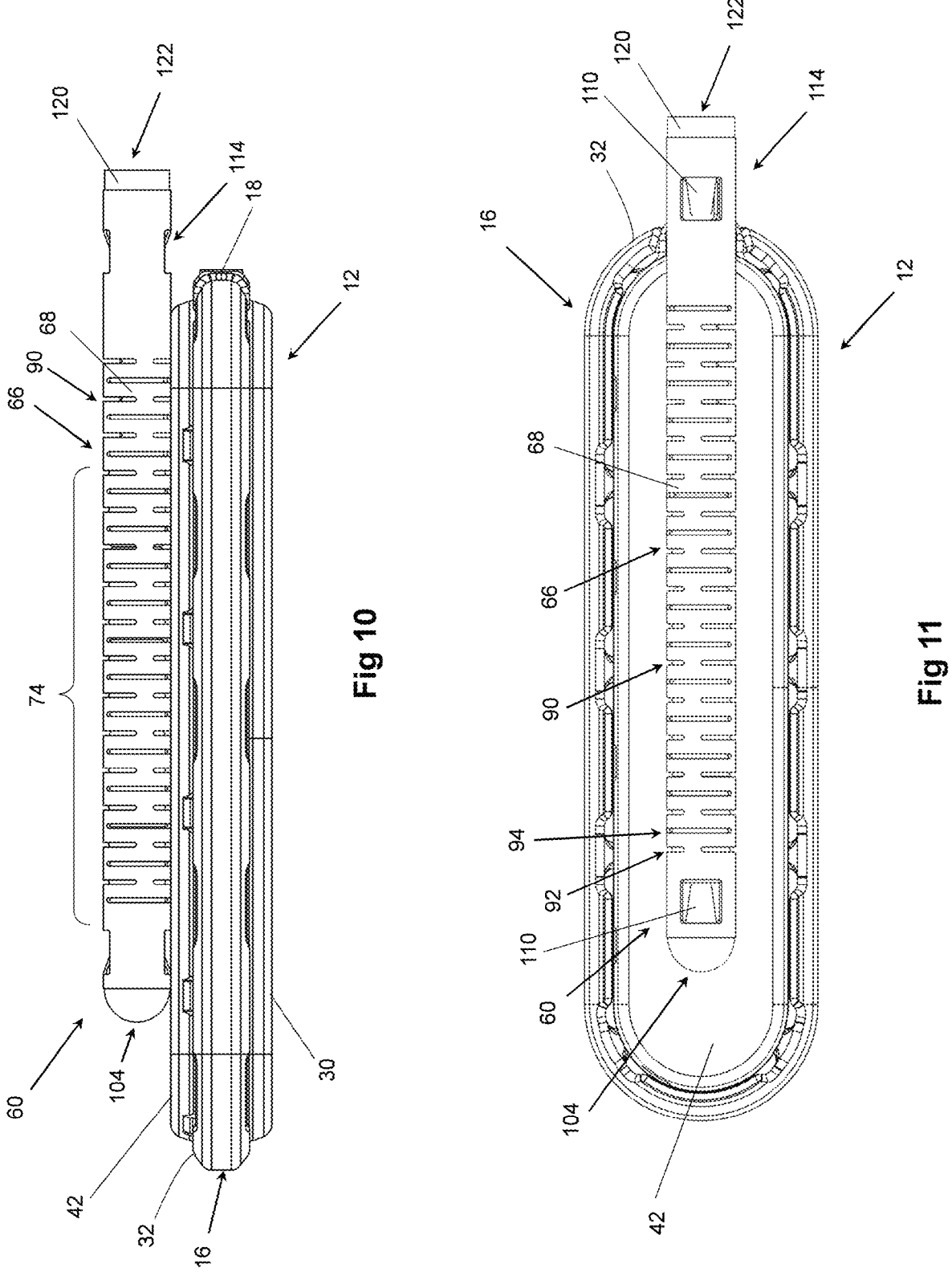
FIG. 10 is a side view of the retrieving device and magnetic implant shown in FIG. 8.
FIG. 11 is a top view of the retrieving device and the magnetic implant shown in FIG. 8.

According to the predetermined pattern shown in FIGS. 9 to 20, the retriever housing slots 90 are provided in an offset configuration. In this offset configuration, a first set 92 of laterally adjacent ones of the retriever housing slots 90 extend along a portion of the circumference of the flexible housing 66 that is different from a second set 94 of laterally adjacent ones of the retriever housing slots 90, the first set 92 of laterally adjacent ones of the retriever housing slots 90 being longitudinally adjacent to the second set 94 of laterally adjacent ones of the retriever housing slots 90, as shown in FIG. 11. In other words, a first set 92 of retriever housing slots 90 is provided spaced-apart from each other and extends along a first arc of the flexible housing 66, and a second set 94 of retriever housing slots 90 is provided spaced-apart from each other and extends along a second arc of the flexible housing 66, the first and second sets 92, 94 of the retriever housing slots 90 being longitudinally spaced-apart from one another.

In the implementation shown, the first set 90 of retriever housing slots comprises a first pair of retriever housing slots 90 and the second set 94 of retriever housing slots 90 comprises a second pair of retriever housing slots 90. The succession of the first set 92 of retriever housing slots 90 and the second set 94 of retriever housing slots 92 is repeated along the longitudinal axis of the retriever housing 60. In FIG. 11, the first set 92 includes fifteen pairs of retriever housing slots 90, and the second set 94 includes fifteen pairs of retriever housing slots 90, for a total of sixty retriever housing slots 90. This predetermined pattern of the retriever housing slots 90 and thus the removal of physical matter at strategic locations around the housing wall 66 can contribute to enable the housing wall 66 to bend or flex in response to an applied force.

In some implementations, the removal of physical matter from the housing wall 66 can be such that the retriever housing slots 90 of the first set 92 of retriever housing slots 90 occupy between about 60% and about 80% of the first arc of the housing wall 68 of the flexible housing 66, and the retriever housing slots 90 of the second set 94 of retriever housing slots 90 occupy between about 60% and about 80% of the second arc of the housing wall 68 of the flexible housing 66.

Figure 19:
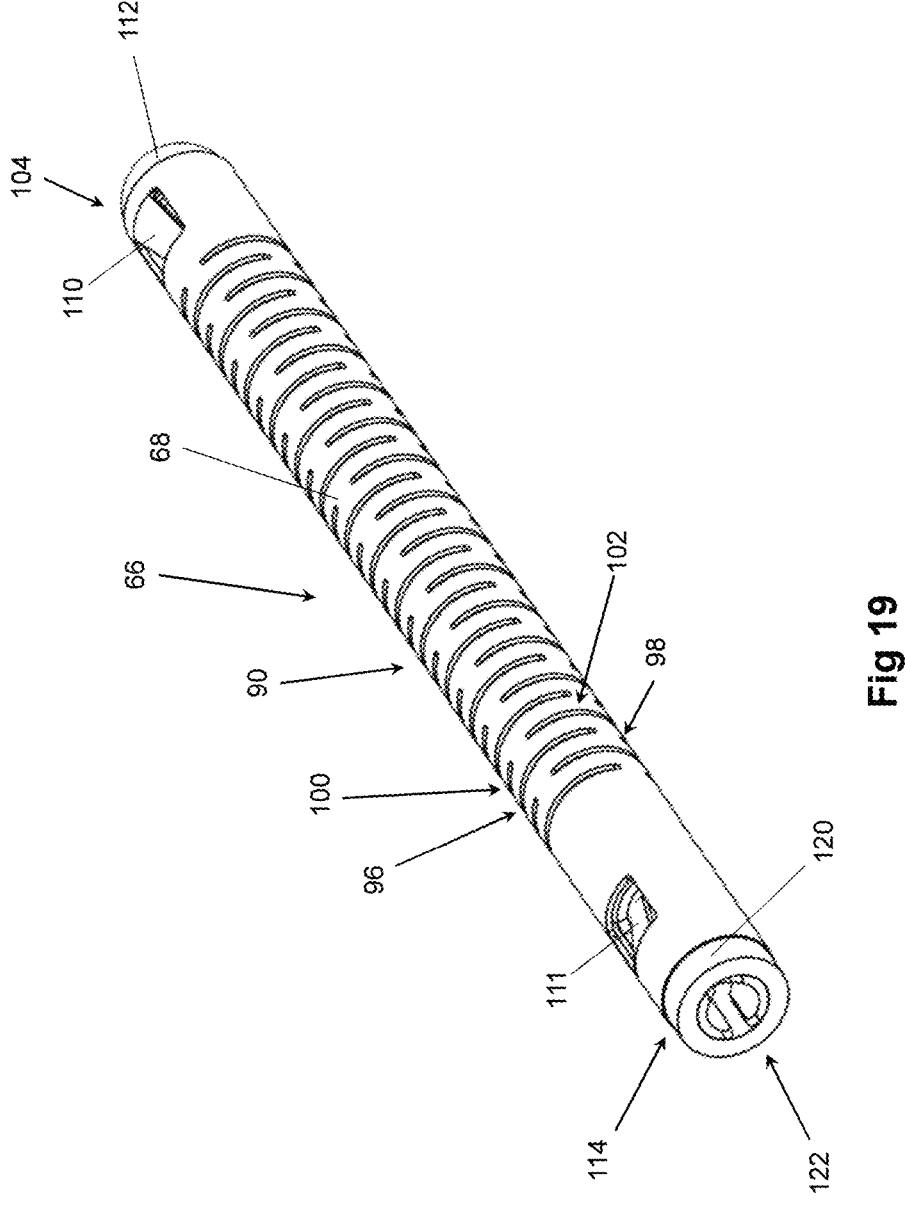
FIG. 19 is a perspective view of the retrieving device of FIG. 8.
Figure 20:
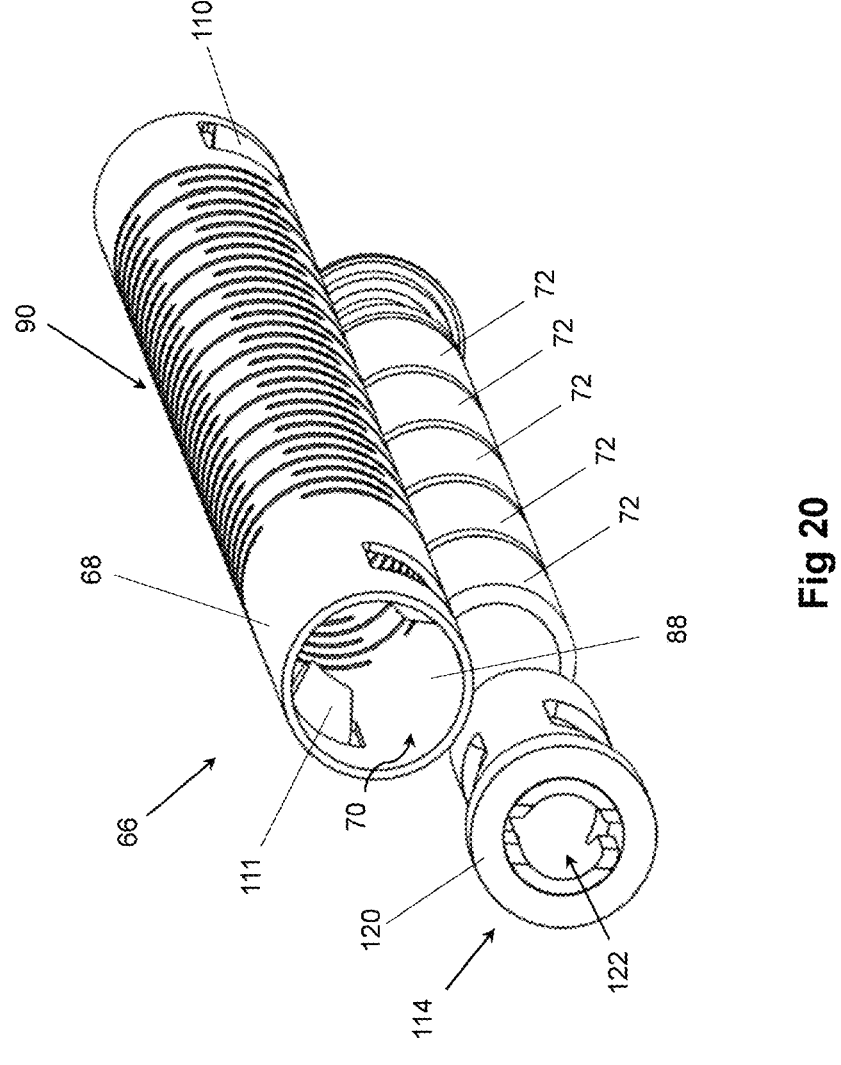
FIG. 20 is an exploded perspective view of the retrieving device of FIG. 8.

Referring more particularly to FIGS. 15, 16 and 19, a first retriever housing slot 96 of the first pair (first set 92) of retriever housing slots 90 extends from about 10 o'clock to about 2 o'clock and a second retriever housing slot 98 of the first pair (first set 92) of retriever housing slots 90 extends from about 4 o'clock to about 8 o'clock. Concomitantly, a first retriever housing slot 98 of the second pair (second set 94) of retriever housing slots 90 extends from about 1 o'clock to about 5 o'clock and a second retriever housing slot 102 of the second pair (second set 94) of retriever housing slots 90 extends from about 7 o'clock to about 11 o'clock. This predetermined pattern of the first and second sets 92, 94 of retriever housing slots 90 repeats itself along the length of the flexible housing 66. In the implementation shown, the same pattern of the first and second sets 92, 94 of retriever housing slots 90 is repeated along the length of the flexible housing 66. It is to be understood that in alternative implementations, the predetermined pattern can include a sub-pattern in a given region of the flexible housing 66, and another sub-pattern in another given region of the flexible housing 66, and so on. This approach can be beneficial for instance if it is desired to provide a given one of the regions of the flexible housing 66 with certain structural characteristics relative to another region of the flexible housing 66. For example, in some implementations, the removal of physical matter can be greater in a region where enhanced flexibility is desired, such as in a central region, distal region or a proximal region of the flexible housing 66.

The predetermined pattern of the retriever housing slots 90 can vary from the one illustrated in FIGS. 9 to 20. For instance, each one of the first and second sets 92, 94 can include a number of retriever housing slots 90 that is different from two. In other words, each one of the first and second sets 92, 94 can include either a single retriever housing slot 90, or more than two retriever housing slots 90. In other implementations, the removal of physical matter from the housing wall 68 of the flexible housing 66 can be achieved differently than with slots. For instance, the housing wall 68 can be a perforated housing wall, with holes that are elongated or not. When the holes are elongated, the elongation can be along a transverse axis of the flexible housing 66, which can contribute to facilitate bending or flexing of the flexible housing in response to an applied force, or along a longitudinal axis of the flexible housing 66.

In some implementations, the removal of physical matter from the housing wall 68 of the flexible housing 66 can be through an entire thickness of the housing wall 68, as shown in FIGS. 9 to 20. In other implementations, the removal of physical matter from the housing wall 68 of the flexible housing 66 can be partial and thus not extend through an entire thickness of the housing wall 68. Leaving a thin layer of the housing wall 68 at selected locations when removal of physical matter has occurred can contribute to maintain the structural integrity of the flexible housing 66 while providing some degree of flexibility.

Figure 26:
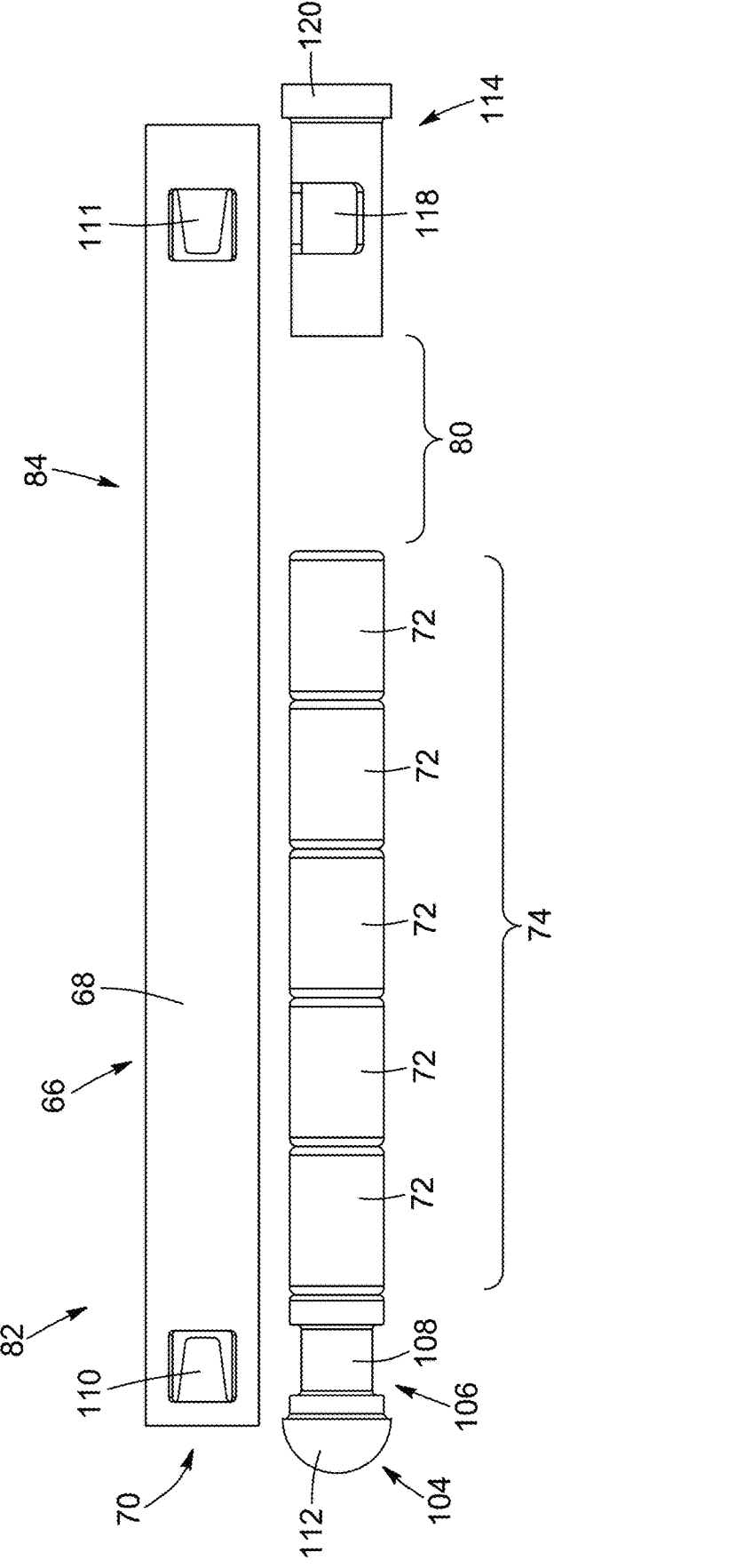
FIG. 26 is an exploded side view of a retrieving device in accordance with another implementation, showing a plurality of retriever magnets, a proximal stopper, a distal plug and a flexible housing made of a flexible material free of retriever housing slots.

In some implementations, the material from which the flexible housing 66 is made can be a flexible material or a non-flexible material. When using the expression "non-flexible material", it is intended to refer to a material that is less flexible than those qualified as flexible materials, and it is to be understood that under a sufficient applied force, there can be some degree of bending that is achieved, nonetheless. In some implementations, the expression "non-flexible material" can be used interchangeably with the expression "rigid material". Examples of non-flexible materials as used herein can include metallic materials such as stainless steel or titanium, for instance, or polymeric material such as polypropylene. In implementations where the flexible housing 66 is made of a non-flexible material and includes retriever housing slots 90, the retriever housing slots 90 can be considered as a main contributor to the flexibility of the flexible housing 66. Examples of flexible materials can include polymeric materials such as rubber and silicone, for instance. When the flexible housing 66 is made of a flexible material, the removal of matter from the housing wall 68 can be omitted, and the flexibility of the flexible housing 66 can be provided by the intrinsic characteristics of the material from which the flexible housing 66 is made. FIG. 26 illustrates an example of a flexible housing 66 made from a flexible material, with the removal of matter from the housing wall 68 being omitted.

In some implementations, the flexible housing 66 can include one or more zones made of a flexible material, and one or more zones made of a non-flexible material, such that the flexibility of the flexible housing 66 can be achieved at selected locations along the length of the flexible housing 66 given the presence of the flexible material, while the remainder of the flexible housing 66 can be made of a non-flexible material. Thus, the flexible housing 66 can be made of any combination of materials that are considered suitable to achieve a desired degree of overall flexibility for the flexible housing 66. For instance, in some implementations, the flexible housing can include a flexible joint made of a flexible material and this provided in a central region of the flexible housing, and the remaining of the flexible housing can be made of a non-flexible material that includes slots (or other types of removal of physical matter) or that does not include retriever housing slots. In such implementations, a second portion of the flexible housing located downstream of the flexible joint can move relative to a first portion of the flexible housing located upstream of the flexible joint, thereby providing flexibility to the overall flexible housing.

It is to be understood that in alternative implementations, the housing of the retrieving device 60 can be non-flexible.

Figure 27:
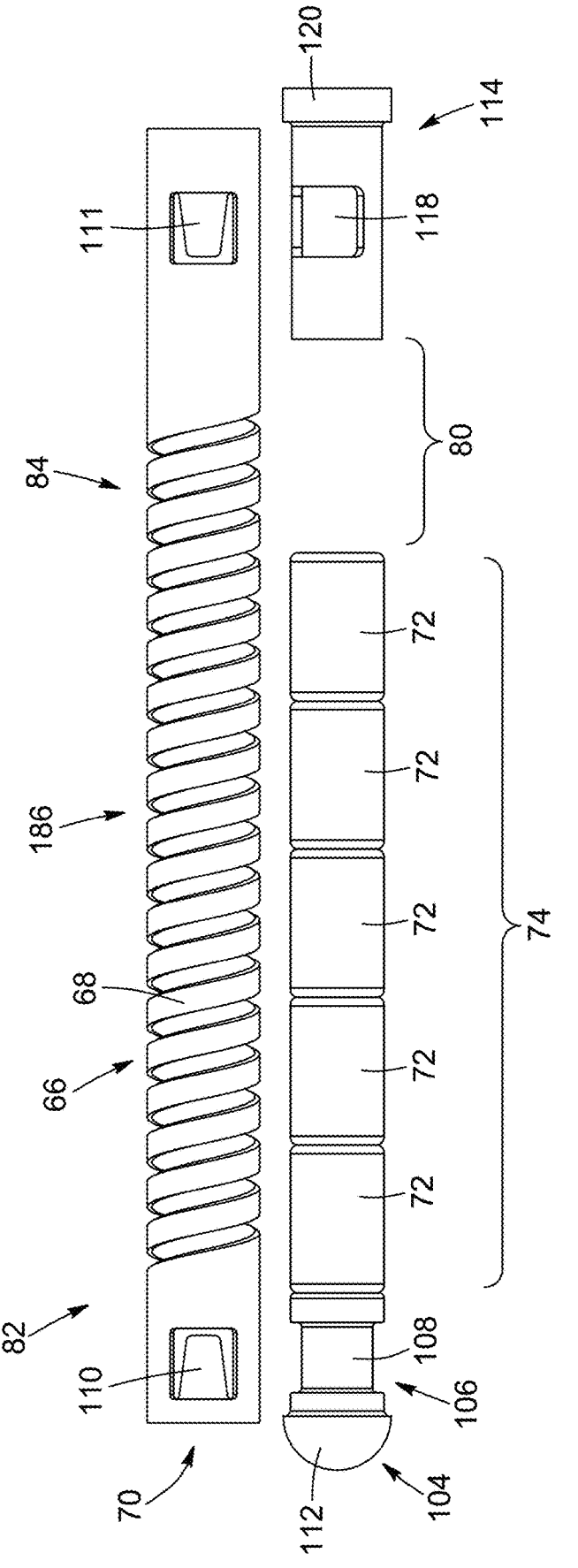
FIG. 27 is an exploded side view of a retrieving device in accordance with another implementation, showing a plurality of retriever magnets, a proximal stopper, a distal plug and a flexible housing shaped as a coil.
Figure 28:
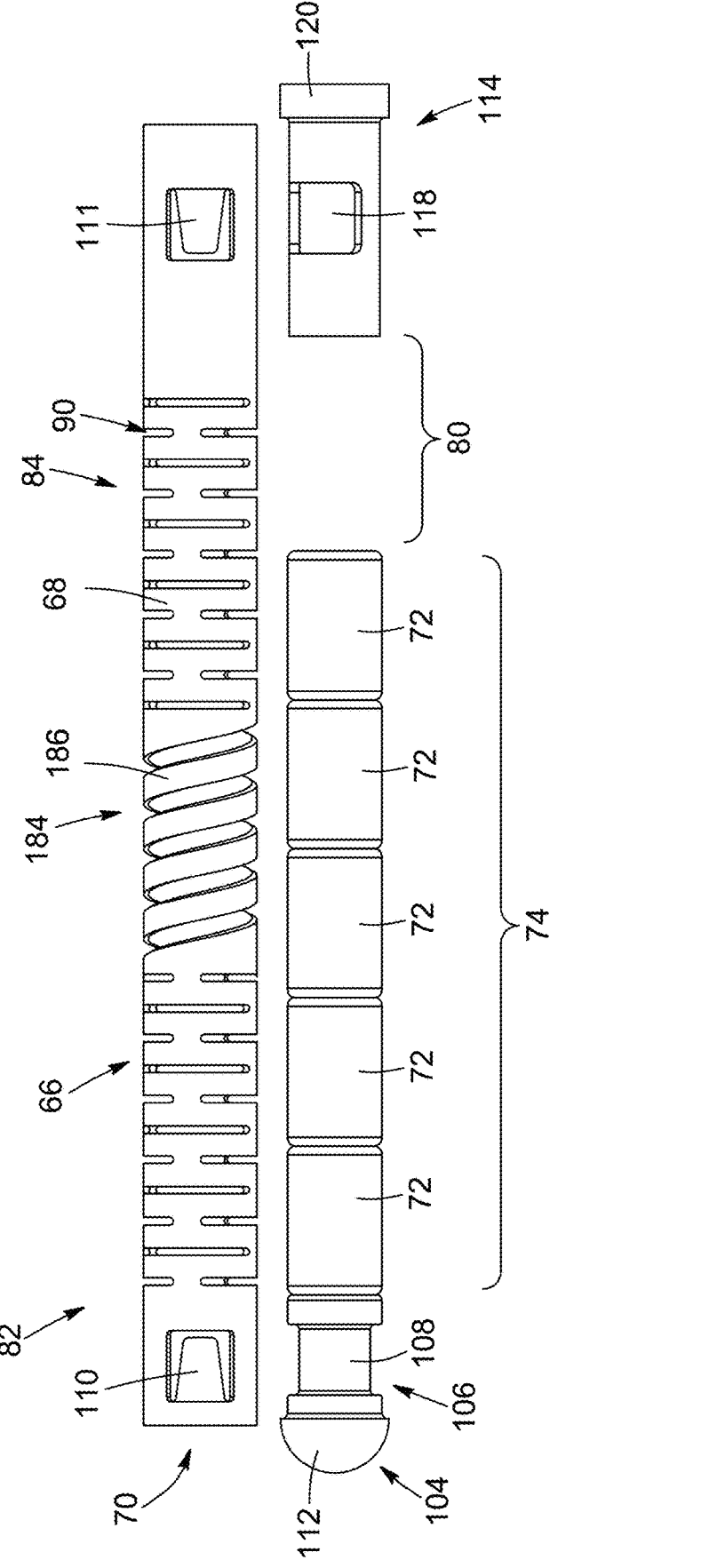
FIG. 28 is an exploded side view of a retrieving device in accordance with another implementation, showing a plurality of retriever magnets, a proximal stopper, a distal plug and a flexible housing including retriever housing slots and a flexible joint shaped as a coil provided in a central region of the flexible housing.
Figure 31:
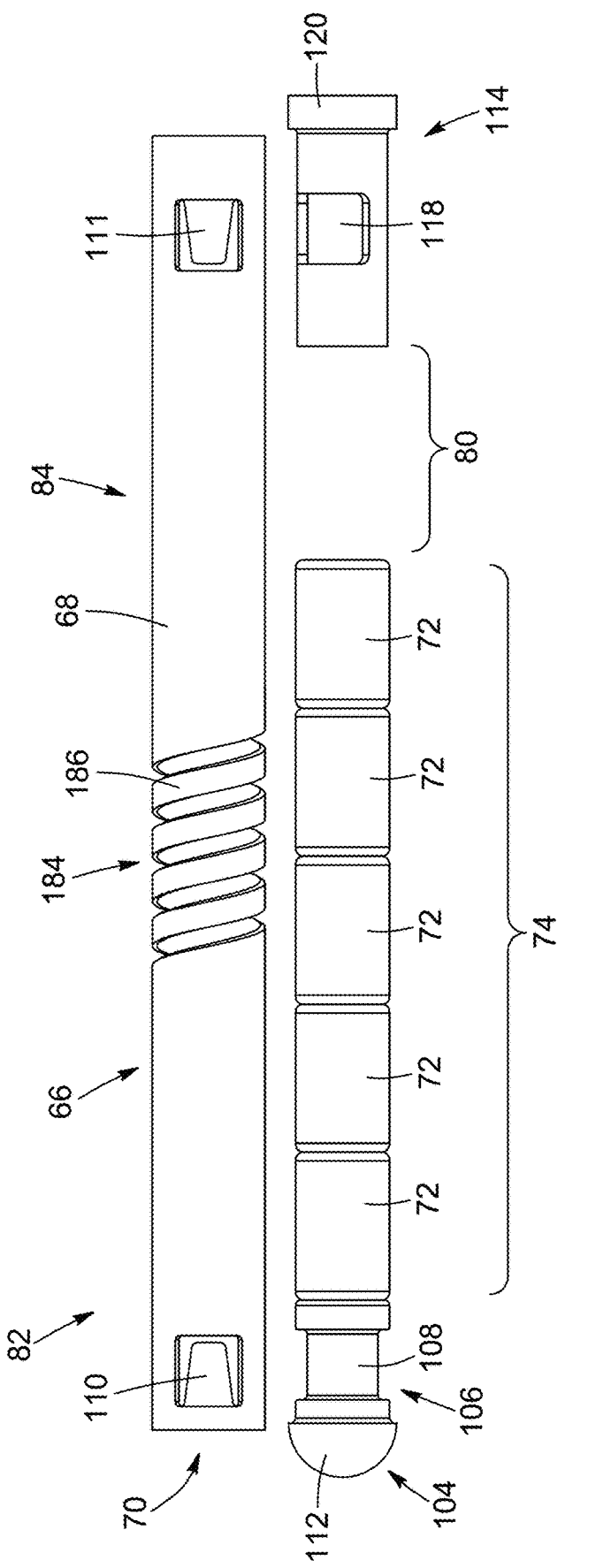
FIG. 31 is an exploded side view of a retrieving device in accordance with another implementation, showing a plurality of retriever magnets, a proximal stopper, a distal plug and a flexible housing without retriever housing slots and a flexible joint shaped as a coil provided in a central region of the flexible housing.

With reference to FIGS. 27, 28 and 31, in some implementations, the flexible housing 66 can include a portion shaped as a coil 186 as shown in FIGS. 28 and 31, or the flexible housing 66 can be shaped as a coil 186 as shown in FIG. 27. For instance, in some implementations, the flexible housing 66 can include a flexible joint 184 shaped as a coil 186 and that is provided in a central region of the flexible housing 66 (or another region such as in the distal region 82 or the proximal region 84), and the remainder of the flexible housing 66 can include retriever housing slots 90 (or other types of removal of physical matter) as shown in FIG. 28. Alternatively, in some implementations, the flexible housing 66 can include a flexible joint 184 shaped as a coil 186 and that is provided in a central region of the flexible housing 66, and the remainder of the flexible housing 66 can be free of retriever housing slots as shown in FIG. 31. It is important to note that the "central region" can be located anywhere along the longitudinal axis of the flexible housing 66, depending on where the flexibility of the flexible housing 66 is desired.

Figure 29:
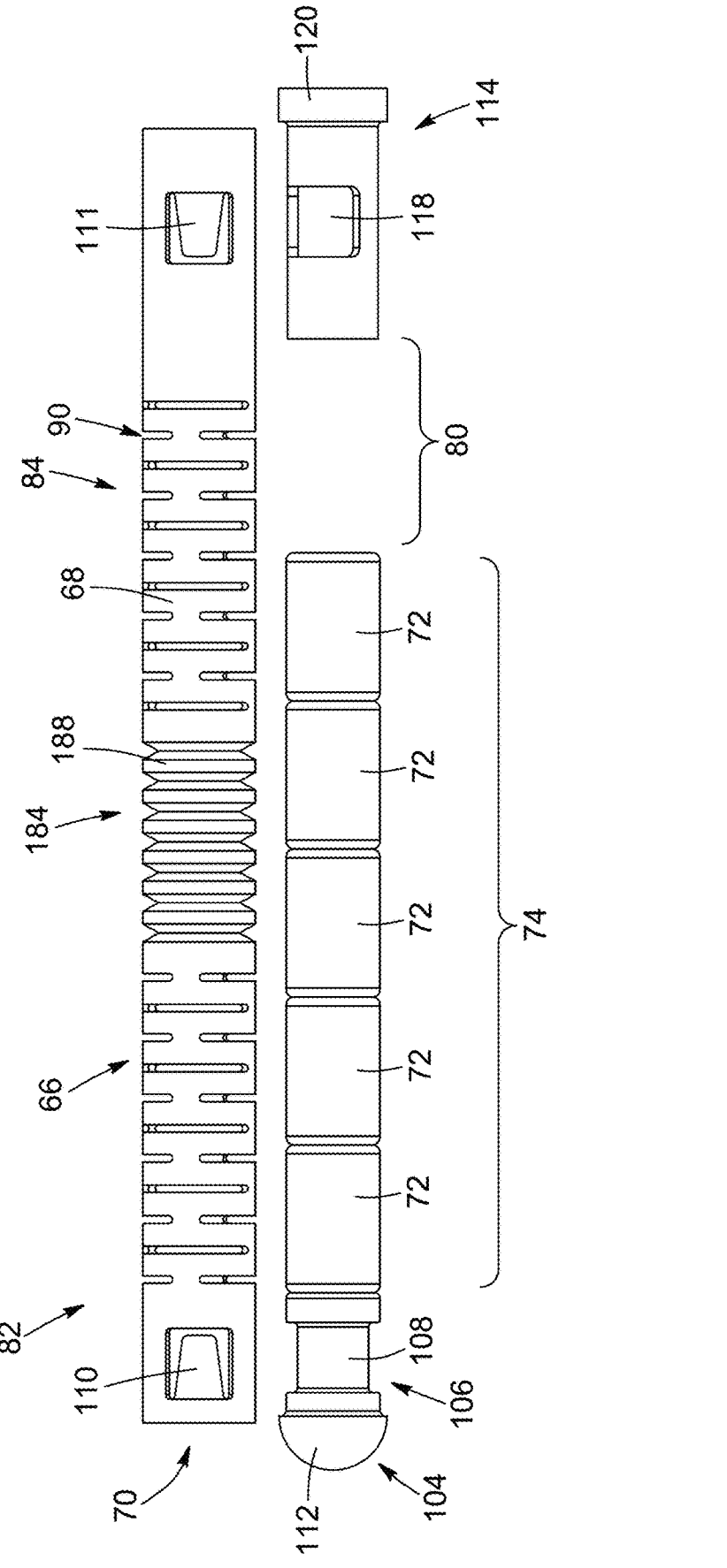
FIG. 29 is an exploded side view of a retrieving device in accordance with another implementation, showing a plurality of retriever magnets, a proximal stopper, a distal plug and a flexible housing including retriever housing slots and a flexible joint that is bellow-shaped provided in a central region of the flexible housing.
Figure 32:
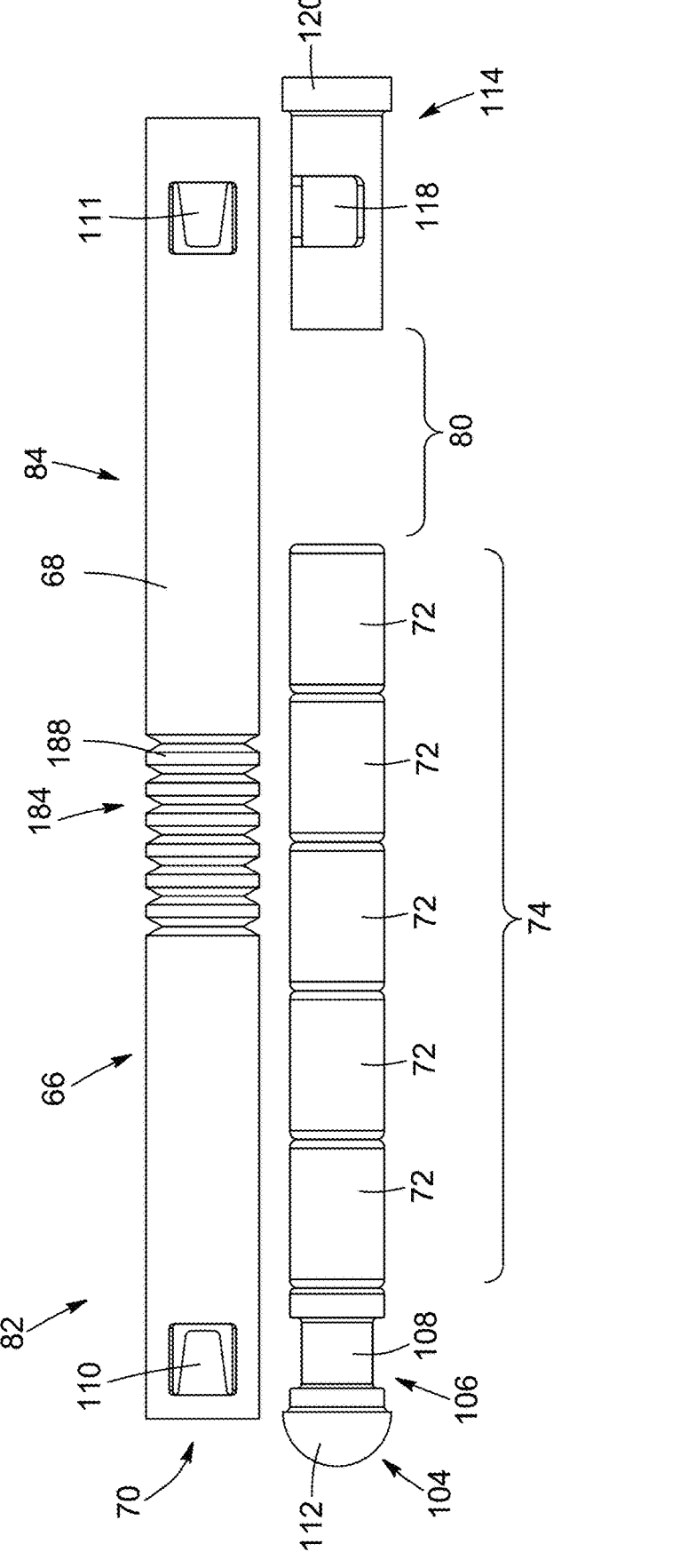
FIG. 32 is an exploded side view of a retrieving device in accordance with another implementation, showing a plurality of retriever magnets, a proximal stopper, a distal plug and a flexible housing without retriever housing slots and a flexible joint that is bellow-shaped provided in a central region of the flexible housing.

In other implementations, the flexible housing 66 can include a flexible joint 184 that is bellow-shaped 188, the flexible joint 184 being provided in a central region of the flexible housing 66 (or another region such as in the distal region 82 or the proximal region 84). The remainder of the flexible housing 66 can include retriever housing slots 90 (or other types of removal of physical matter) as shown in FIG. 29, or the remainder of the flexible housing 66 can be free of retriever housing slots as shown in FIG. 32.

Figure 30:
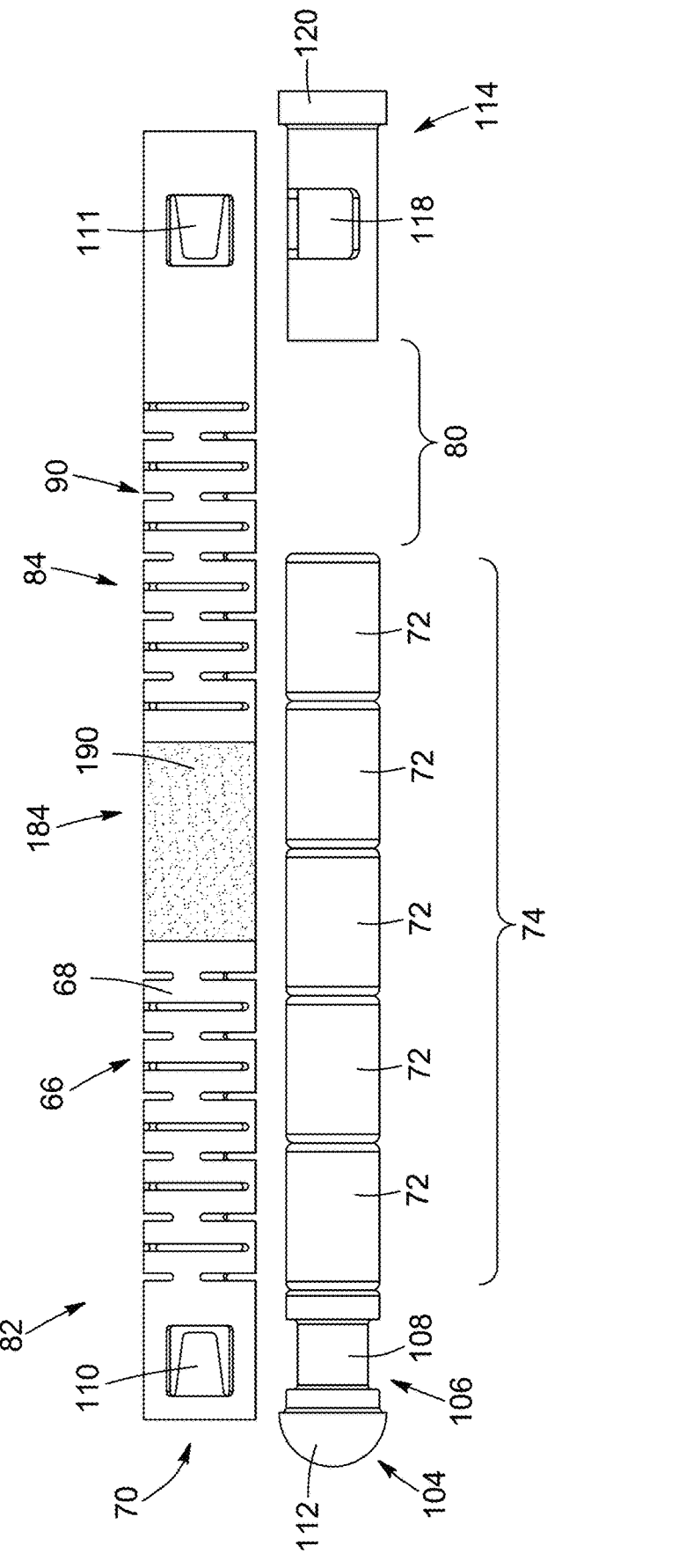
FIG. 30 is an exploded side view of a retrieving device in accordance with another implementation, showing a plurality of retriever magnets, a proximal stopper, a distal plug and a flexible housing including retriever housing slots and a flexible joint comprising a flexible material provided in a central region of the flexible housing.
Figure 33:
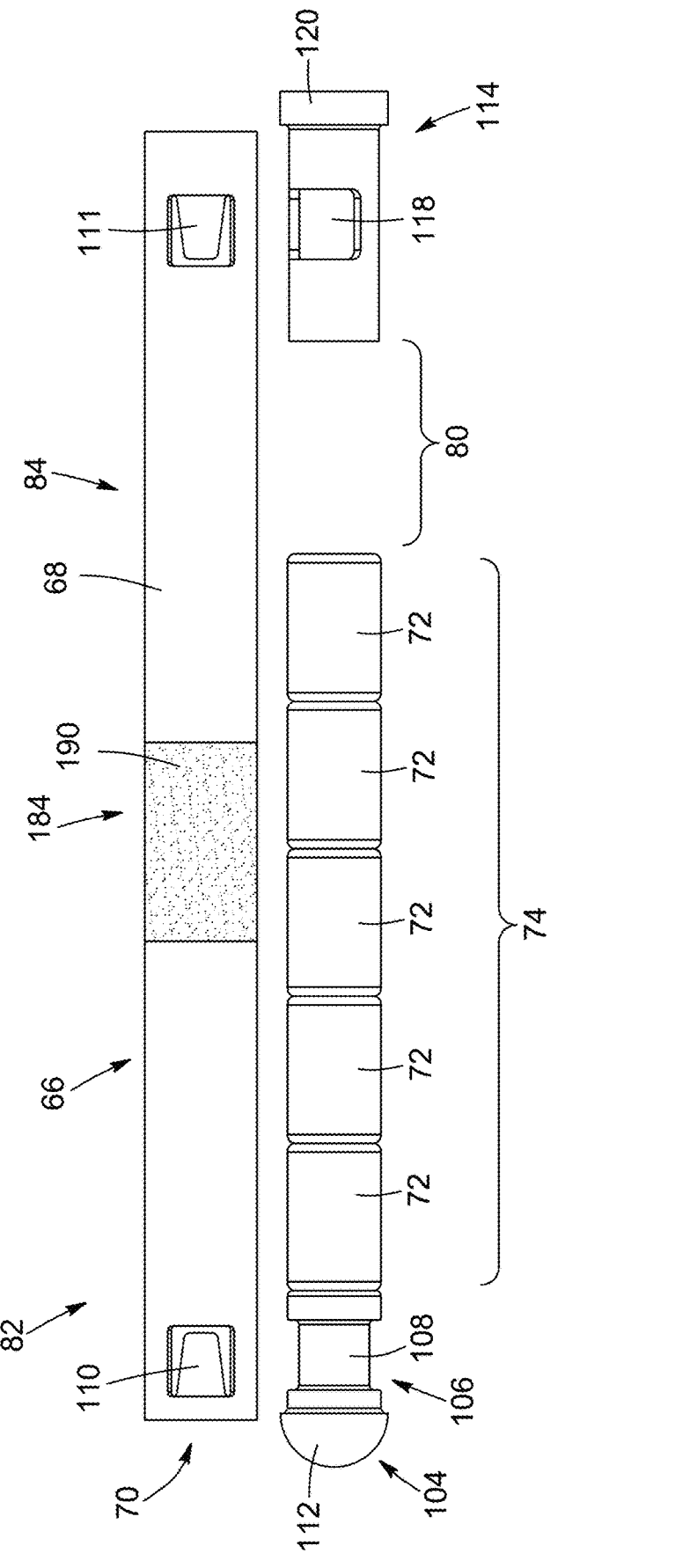
FIG. 33 is an exploded side view of a retrieving device in accordance with another implementation, showing a plurality of retriever magnets, a proximal stopper, a distal plug and a flexible housing free of retriever housing slots and a flexible joint comprising a flexible material different from the flexible housing, the flexible joint being provided in a central region of the flexible housing.

In yet other implementations, the flexible housing 66 can include a flexible joint 184 made of a flexible joint material 190 that is different from the material from which the remainder of the housing wall 68 is made, the flexible joint 184 being provided in a central region of the flexible housing 66 (or another region such as in the distal region 82 or the proximal region 84). The remainder of the flexible housing 66 can includes retriever housing slots (or other types of removal of physical matter) as shown in FIG. 30, or the remainder of the flexible housing 66 can be free of retriever housing slots as shown in FIG. 33.

In such implementations, the distal region 82 of the flexible housing, located distally from the flexible joint 184, can move relative to the proximal region 84 of the flexible housing located upstream of the flexible joint 184, thereby providing flexibility to the overall flexible housing 66. In other words, the flexible housing 66 can include a first portion located upstream of the flexible joint 184 and a second portion located downstream of the flexible joint 184, the flexible joint 184 being provided in a central region of the flexible housing 66 (or another region such as in the distal region 82 or the proximal region 84). In such implementations, the retriever magnets 72 can be received in the retriever magnet receiving cavity 70 of the distal region 82 and proximal region 84 of the flexible housing 66, and optionally within the retriever magnet receiving cavity 70 defined by the coil 186. In some implementations, at least one of the first and second portions of the flexible housing 66 can include a non-flexible material.

When retriever magnets 72 are received in the retriever magnet receiving cavity 70 defined by the coil 186, the retriever magnets 72 can be provided in an end-to-end fashion and the number of retriever magnets 72 can be chosen such that the coil 186 can bend under an applied force. In some implementations, when the flexible housing 66 is entirely made of a coil as shown in FIG. 27, the retriever magnets 72 are received in the retriever magnet receiving cavity 70 defined by the coil 72 in an end-to-end fashion, and the number of retriever magnets 72 can be chosen such that the coil 186 can bend under an applied force.

It is to be understood that although the "central region" is used hereinabove to locate the flexible joint 184 along the longitudinal axis of the flexible housing 66, the flexible joint 184 can alternatively be located at any location along the longitudinal axis of the flexible housing 66 that is deemed suitable for providing the desired flexibility to the flexible housing 66, and more particularly to provide movement of a second portion of the flexible housing located downstream of the flexible joint 184 relative to a first portion of the flexible housing located upstream of the flexible joint 184, thereby providing flexibility to the overall flexible housing 66.

Additional Features of the Retrieving Device

Still referring to FIGS. 9 to 20, and more particularly to FIG. 12, the retrieving device 60 further comprises a distal plug 104 provided at a distal end of the flexible housing 66. The distal plug 104 includes a flexible housing engaging portion 106 configured for insertion into the retriever magnet receiving cavity 70 of the flexible housing 66. In the implementation shown, the flexible housing engaging portion 106 includes a plug recess 108 configured to engage inwardly extending distal protrusions 110 of the flexible housing 66, the inwardly extending distal protrusions 110 of the flexible housing 66 extending inwardly from the inner surface 88 of the housing wall 68 of the flexible housing 66 and into the retriever magnet receiving cavity 70, in the distal region 82 thereof. The flexible housing engaging portion 106 of the distal plug 104 can thus be inserted into the retriever magnet receiving cavity 70 of the flexible housing 66 in a snap-fit configuration. The distal plug 104 further includes a plug head 112 having a diameter that enables abutment against the distal extremity 67 of the housing wall 66. Although the distal plug 104 is exemplified as being a distinct element from the housing wall 68, it is to be understood that in alternative implementations, the distal plug and the housing wall can be integral to each other, i.e., can form a single piece. In such implementations, the inwardly extending distal protrusions 110 provided in the distal region 82 of the flexible housing 66 can be omitted. Furthermore, when the distal plug 104 and the housing wall 68 are provided as distinct elements, there can be other types of engagements than a snap-fit, as long as the cooperation of the distal plug 104 with the housing wall 68 enables the distal plug 104 to remain in position and engaged with the housing wall 68. The distal plug 104 generally includes atraumatic features to facilitate navigation of the retrieving device 60 through the digestive tract without causing trauma to the lining of the digestive tract. In the implementation shown, the distal plug 104 can be considered to be dome-shaped.

Still referring to FIGS. 9 to 20, the retrieving device 60 further comprises a proximal stopper 114 provided at a proximal end of the flexible housing 66. Similarly to the distal plug 104, the proximal stopper 114 includes a flexible housing engaging portion 116 configured for insertion into the retriever magnet receiving cavity 70 of the flexible housing 66. In the implementation shown, the flexible housing engaging portion 116 includes a stopper recess 118 configured to engage inwardly extending proximal protrusions 111 of the flexible housing 66, the inwardly extending proximal protrusions 111 of the flexible housing 66 extending inwardly from the inner surface 88 of the housing wall 68 of the flexible housing 66, i.e., into the retriever magnet receiving cavity 70, in the proximal region 84 thereof. The flexible housing engaging portion 116 of proximal stopper 114 can thus be inserted into the retriever magnet receiving cavity 70 of the flexible housing 66 in a snap-fit configuration. The proximal stopper 114 further includes a proximal stopper rim 120 having a diameter that enables abutment against the proximal extremity 69 of the housing wall 66. Although the proximal stopper 114 is exemplified as being a distinct element from the housing wall 68, it is to be understood that in alternative implementations, the proximal stopper 114 and the housing wall 68 can be integral to each other, i.e., can form a single piece. In such implementations, the inwardly extending proximal protrusions 111 provided in the proximal region 84 of the flexible housing 66 can be omitted. Furthermore, when the proximal stopper 114 and the housing wall 68 are provided as distinct elements, there can be other types of engagements than a snap-fit, as long as the cooperation of the proximal stopper 114 with the housing wall 68 enables the proximal stopper 114 to remain in position and engaged with the housing wall 68. The proximal stopper 114 further includes a delivery attachment 122 configured for attachment, or engagement, with the delivery wire 62. The configuration of the delivery attachment 122 can be any suitable configuration that enables the retrieving device 60 to be engaged with the delivery wire 62. Alternatively, the proximal stopper 114 itself can be configured for engagement with the delivery wire 62, whether the proximal stopper 114 is integral with the housing wall 68 or the proximal stopper 114 and the housing wall 68 are distinct elements. The distal plug 104 together with the proximal stopper 114 contribute to enclose the retriever magnets 72 within the retriever magnet receiving cavity 70.

Figure 21:
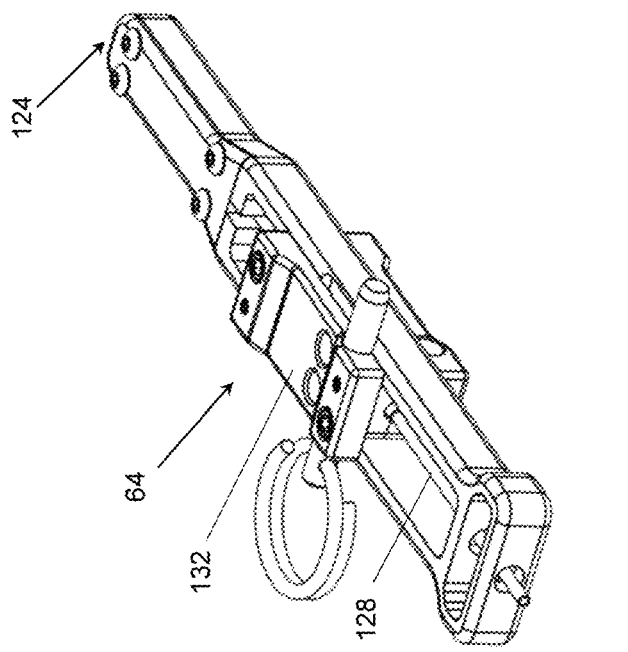
FIG. 21 is a perspective view of the handle of FIG. 8.

With reference to FIGS. 8 and 21 and as mentioned above, the delivery wire 62 is connected to a handle 64 that can be manipulated by a healthcare provider. The handle 64 includes a delivery wire receiving portion 124 that is configured for receiving a delivery wire proximal end 126 of the delivery wire 62. In the implementation shown, the delivery wire 62 includes a delivery wire core 128 and a delivery wire outer shell 130. The delivery wire core 128 and the delivery wire outer shell 130 together extend within a distal portion of the handle 64, and upstream from the distal portion of the handle 64, i.e., towards the healthcare provider, only the delivery wire core 128 remains and extends out of the proximal end of the handle 64. It is to be understood that the handle 64, and the cooperation of the delivery wire 62 and the handle 64, can take any suitable configuration that enables the healthcare provider to insert the retrieving device 60 within the digestive tract of the patient and navigate the retrieving device 60 toward the magnetic implant to retrieve.

As described above with respect to the delivery wire 62 of the retrieving device 60, the handle 64 of the retrieving device 60 can be the same, or can include similar features, as the handle of a delivery catheter used to deliver the magnetic implant at the desired site of the anastomosis, such as the deliver catheter 20 exemplified in FIG. 1. Accordingly, the delivery attachment 122 of the retrieving device 60 can be configured similarly to the connecting member 18 of the magnetic implant, such that the same delivery catheter can be interchangeably engaged with the magnetic implant 12, 14 and with the retrieving device 60. The handle 64 contains a slide 132 operatively engaged with the connected to the delivery wire core 128, which can also be referred to as a drive cable. The delivery wire core 128 can then be used to actuate the delivery attachment 122, or interconnecting mechanism, that locks and unlocks the delivery wire 62 to the retrieving device 60, or the magnetic implant.

23

Method for Retrieving a Magnetic Implant of a Pair of
Magnetic Implants Configured to Forming an Anastomosis
in the Digestive System A method for retrieving a selected one of first and second
magnetic implants used for forming an anastomosis between
two adjacent walls of a digestive system of a patient will
now be described in further detail.

The method includes inserting the first magnetic implant
into the digestive tract via a mouth of the patient so that the
first magnetic implant can travel through the digestive tract
and eventually reach a first hollow organ. Inserting the first
magnetic implant into the digestive tract via the mouth of the
patient can involve the patient swallowing the first magnetic
implant as would typically be done for food. Natural pro-
cesses associated with digestion can take place following the
swallowing of the first magnetic implant, which induce the
travelling of the first magnetic implant down the digestive
tract. The delivery of the first magnetic implant to the first
hollow organ can thus rely on such natural processes, such
as peristalsis, thereby alleviating the need for manipulating
an endoscope to navigate the first magnetic implant through
the digestive tract and deliver the first magnetic implant to
the first hollow organ. Alternatively, inserting the first mag-
netic implant into the digestive system via the mouth of the
patient can also involve the use of an endoscope, or another
surgical instrument, if deemed appropriate by the healthcare
provider, for instance in cases when a more rapid delivery of
the first magnetic implant to the first hollow organ is desired.

The method also includes delivering the second magnetic
implant to a second location on another side of the desired
anastomose site. Various techniques can be used to navigate,
or deliver, the second magnetic implant to the desired site of
the anastomosis. It is to be noted that a chosen technique for
navigating or deliver the first magnetic implant can be the
same or different relative to the chosen technique for navigating or deliver the second magnetic implant. Thus, in some
implementations, the second magnetic implant can be deliv-
ered to the second location on the other side of the desired
anastomosis side using the same techniques as presented
above regarding the delivery of the first magnetic implant to
the target location. In such implementations, the patient may
be asked to swallow the first magnetic implant at a given
time, and then asked to swallow the second magnetic
implant after a predetermined period of time, such that each
one of the first and second magnetic implants can reach a
first target location and a second target location, respec-
tively, at moments that are suitable for the procedure. With
such an approach, the second hollow organ and thus the
second target location would be located downstream of the
first hollow organ and thus of the first target location.

In implementations where the second magnetic implant is
delivered at the second location on the other side of the
desired site of the anastomosis by a technique that is
different than the techniques described above for delivering
the first magnetic implant to the target location, i.e., at the
first location, delivering the second magnetic implant can
include releasably engaging the second magnetic implant
with a delivery catheter insertable in a working channel of
a corresponding endoscope via a connecting member, for
instance. The endoscope (or colonoscope) can then be used
to introduce the second magnetic implant into the digestive
tract and to deliver the second magnetic implant at the
second location.

In some implementations, the second magnetic implant
can be navigated to the second location using a laparoscopic
procedure. Details regarding various types of suitable lapa-
roscopic procedures and laparoscopic instruments and devices can be found described in U.S. Patent Application
Nos. 2020/0138438 and 2022/0087678, which are incorpo-
rated herein by reference in their entirety.

At any time following the insertion of the first magnetic
implant into the digestive tract or following the insertion of
the second magnetic implant into the digestive tract, if it is
determined that the first magnetic implant or the second
magnetic implant (if applicable) is not navigated accurately
at the site of the desired anastomosis, does not reach the site
of the desired anastomosis, or if there is an unexpected
disengagement between the magnetic implant being deliv-
ered and the delivery instrument used to deliver the mag-
netic implant, the retrieving device as described herein can
be used to magnetically engage with the magnetic implant to
retrieve, to either reposition the magnetic implant at the
desired site of the anastomosis or retrieve the magnetic
implant out of the patient. In order to do so, the healthcare
provider can use the handle and delivery wire to introduce
the retrieving device into the digestive tract of the patient. In
some implementations, the delivery wire and handle can be
used in cooperation with an endoscope, with the delivery
wire being received in a working channel of the endoscope,
as exemplified in FIG. 24. Alternatively, the handle and
delivery wire can be used on their own to navigate the
retrieving device. The healthcare provider can then navigate
the retrieving device along the digestive tract to the location
where the magnetic implant to retrieve is. When the retriev-
ing device and the magnetic implant to retrieve are in
sufficiently close proximity to each other, the magnetic
attraction between the retrieving device, i.e., the retriever
magnets, and the magnetic implant enables the magnetic
engagement of the retrieving device with the magnetic
implant. Given the configuration of the retrieving device, the
retrieving device can be docked for instance against a main
surface of the magnetic implant, or any other surface of the
magnetic implant, potentially without having a visual of the
magnetic implant to retrieve given the magnetic attraction
between the retrieving device and the magnetic implant, and
without having to further engage a loop, a hook or another
type of engagement feature that could be provided on the
magnetic implant.

The magnetic attraction between the retrieving device and
the magnetic implant can be sufficiently strong that the
healthcare provider can pull on the delivery wire to modify
the location of the magnetic implant, either to one side of the
desired anastomosis or out of the patient. In implementa-
tions where the magnetic implant is retrieved out of the
patient, the magnetic implant can subsequently be reintro-
duced into the digestive tract using any suitable technique,
such as those described above.

Several alternative implementations and examples have
been described and illustrated herein. The implementations
of the technology described above are intended to be exem-
plary only. A person of ordinary skill in the art would
appreciate the features of the individual implementations,
and the possible combinations and variations of the com-
ponents. A person of ordinary skill in the art would further
appreciate that any of the implementations could be pro-
vided in any combination with the other implementations
disclosed herein. It is understood that the technology may be
embodied in other specific forms without departing from the
central characteristics thereof. The present implementations
and examples, therefore, are to be considered in all respects
as illustrative and not restrictive, and the technology is not
to be limited to the details given herein. Accordingly, while
the specific implementations have been illustrated and
described, numerous modifications come to mind.

Other possible item(s), aspect(s), object(s), embodiment(s), variant(s), item(s) and/or advantage(s) of the present disclosure/invention, all being preferred and/or optional, are briefly summarized hereinbelow:

1. A retrieving device for insertion within a digestive tract of a patient, the retrieving device comprising:
   a flexible housing having a proximal portion engageable with a delivery wire and a distal portion opposite the proximal portion, the flexible housing comprising:
   a housing wall defining a retriever magnet receiving cavity; and
   a plurality of retriever magnets provided in series within the retriever magnet receiving cavity;
   wherein the retrieving device is magnetically engageable with a first magnetic implant of a pair of magnetic implants configured for forming an anastomosis between two adjacent walls of the digestive tract of the patient.

2. The retrieving device of item 1, wherein the housing wall of the flexible housing defines retriever housing slots extending laterally around a portion of the housing wall.

3. The retrieving device of item 1, wherein the flexible housing is tubular, and the housing wall of the flexible housing defines retriever housing slots extending circumferentially around a portion of the housing wall.

4. The retrieving device of item 2 or 3, wherein longitudinally adjacent ones of the retriever housing slots are provided in an offset configuration.

5. The retrieving device of item 3, wherein the retriever housing slots comprise:
   a first set of retriever housing slots provided spaced-apart from each other and extending along a first arc of the flexible housing; and
   a second set of retriever housing slots provided spaced-apart from each other and extending along a second arc of the flexible housing, the first and second sets of the retriever housing slots being longitudinally spaced-apart from one another.

6. The retrieving device of item 5, wherein the first set of retriever housing slots comprises a first pair of retriever housing slots and the second set of retriever housing slots comprises a second pair retriever housing slots.

7. The retrieving device of item 6, wherein a first retriever housing slot of the first pair of retriever housing slots extends from about 10 o'clock to about 2 o'clock and a second retriever housing slot of the first pair of retriever housing slots extends from about 4 o'clock to about 8 o'clock.

8. The retrieving device of item 7, wherein a first retriever housing slot of the second pair of retriever housing slots extends from about 1 o'clock to about 5 o'clock and a second retriever housing slot of the second pair of retriever housing slots extends from about 7 o'clock to about 11 o'clock.

9. The retrieving device of any one of items 5 to 8, wherein the retriever housing slots of the first set of retriever housing slots extend between about 60% and about 80% of the first arc of the flexible housing.

10. The retrieving device of any one of items 5 to 9, wherein the retriever housing slots of the second set of retriever housing slots extend between about 60% and about 80% of the second arc of the flexible housing.

11. The retrieving device of any one of items 1 to 10, wherein the flexible housing comprises a flexible material.

12. The retrieving device of item 11, wherein the flexible material comprises a polymeric material.

13. The retrieving device of item 12, wherein the polymeric material comprises one or more of silicon and rubber.

14. The retrieving device of any one of items 1 to 13, wherein the flexible housing comprises a non-flexible material.

15. The retrieving device of item 14, wherein the non-flexible material comprises a metal.

16. The retrieving device of item 15, wherein the metal comprises one or more of stainless steel and titanium.

17. The retrieving device of any one of items 1 to 16, wherein the flexible housing comprises a flexible joint.

18. The retrieving device of item 17, wherein the flexible joint comprises a coil, is bellow-shaped or comprises a flexible material.

19. The retrieving device of item 18, wherein the flexible housing comprises a first portion upstream of the flexible joint and a second portion downstream of the flexible joint, the flexible joint being provided in a central region of the flexible housing.

20. The retrieving device of item 19, wherein at least one of the first and second portions of the flexible housing comprises a non-flexible material.

21. The retrieving device of item 1, wherein the flexible housing is shaped a coil.

22. The retrieving device of any one of items 1 to 21, wherein the retriever magnets are shaped as substantially spherical beads or have a cylindrical shape.

23. The retrieving device of any one of items 1 to 22, wherein the retriever magnets are distributed within the retriever magnet receiving cavity to define a non-magnetic portion and a magnetic portion of the retrieving device.

24. The retrieving device of item 23, wherein a length ratio between a length of the magnetic portion and a length of the non-magnetic portion is between about 10:1 to about 2:1.

25. The retrieving device of item 23, wherein a length ratio between a length of the magnetic portion and a length of the non-magnetic portion is about 4:1.

26. The retrieving device of any one of items 1 to 25, further comprising a distal plug at the distal portion of the flexible housing, the distal plug being engageable with the distal portion of the flexible housing to maintain the plurality of retriever magnets within the retriever magnet receiving cavity.

27. The retrieving device of item 26, wherein the flexible housing comprises inwardly extending distal protrusions configured to engage the distal plug.

28. The retrieving device of any one of items 1 to 25, further comprising a distal plug at a distal portion of the flexible housing, the distal plug being integral with the distal portion of the flexible housing to maintain the plurality of retriever magnets within the retriever magnet receiving cavity.

29. The retrieving device of any one of items 26 to 28, wherein the distal plug has atraumatic features.

30. The retrieving device of any one of items 26 to 29, wherein the distal plug is dome-shaped.

31. The retrieving device of any one of items 1 to 30, further comprising a proximal stopper at the proximal portion of the flexible housing, the proximal stopper being engageable with the proximal portion of the flexible housing to maintain the plurality of retriever magnets within the retriever magnet receiving cavity.

32. The retrieving device of item 31, wherein the flexible housing comprises inwardly extending proximal protrusions configured to engage the proximal stopper.

33. The retrieving device of any one of items 1 to 30, further comprising a proximal stopper at the proximal portion of the flexible housing, the proximal stopper being integral with the flexible housing to maintain the plurality of retriever magnets within the retriever magnet receiving cavity 34. The retrieving device of any one of items 31 to 33, wherein the proximal stopper is engageable with the delivery wire.

35. The retrieving device of any one of items 31 to 33, wherein the proximal stopper comprises a delivery attachment engageable with the delivery wire.

36. The retrieving device of any one of items 1 to 35, wherein the retrieving device is magnetically engageable with the first magnetic implant by contacting a main surface of the first magnetic implant.

37. The retrieving device of any one of items 1 to 36, wherein a magnetic strength of the plurality of retriever magnets is selected such that a magnetic attraction between the retrieving device and the first magnetic implant enables displacement of the first magnetic implant along the digestive tract of the patient.

38. The retrieving device of any one of items 1 to 37, wherein the delivery wire is connected to a handle manipulable by a healthcare provider.

39. A system for retrieving a first magnetic implant of a pair of magnetic implants configured for forming an anastomosis between two adjacent walls of a digestive tract of a patient, the system comprising:

a retrieving device for insertion within a digestive tract of a patient, the retrieving device comprising:
a flexible housing having a proximal portion and a distal portion opposite the proximal portion, the flexible housing comprising:
a housing wall defining a retriever magnet receiving cavity; and
a plurality of retriever magnets provided in series within the retriever magnet receiving cavity;
a delivery wire engageable with the proximal portion of the flexible housing; and
a handle engageable with the delivery wire;
wherein the retrieving device is magnetically engageable with the first magnetic implant of the pair of magnetic implants within the digestive tract when brought in sufficiently close proximity of each other via manipulation of the delivery wire.

40. The system of item 39, further comprising one or more features as defined in any one of items 2 to 38.

41. The retrieving device of item 39 or 40, wherein the delivery wire comprises a delivery wire inner core and a delivery wire outer shell.

42. A system for forming an anastomosis between two adjacent walls of a digestive tract of a patient, the system comprising:
first and second magnetic implants configured to magnetically couple to each other through the two adjacent walls of the digestive tract at a desired site of the anastomosis to compress a portion of the two adjacent walls therebetween and form a necrotic area that becomes surrounded by a scarred edge following a healing time period; and a retrieving device for insertion within a digestive tract of a patient, the retrieving device comprising:
a flexible housing having a proximal portion engageable with a delivery wire and a distal portion opposite the proximal portion, the flexible housing comprising:
a housing wall defining a retriever magnet receiving cavity; and
a plurality of retriever magnets provided in series within the retriever magnet receiving cavity;
wherein the retrieving device is magnetically engageable with a first magnetic implant of a pair of magnetic implants configured for forming an anastomosis between two adjacent walls of the digestive tract of the patient.

43. The system of item 42, further comprising one or more features as defined in any one of items 2 to 38.

44. A retrieving device for insertion within a digestive tract of a patient, the retrieving device comprising:
a housing having a proximal portion engageable with a delivery wire and a distal portion opposite the proximal portion, the housing comprising:
a housing wall defining a retriever magnet receiving cavity;
a retriever magnet provided in series within the retriever magnet receiving cavity;
wherein the retrieving device is magnetically engageable with a first magnetic implant of a pair of magnetic implants configured for forming an anastomosis between two adjacent walls of the digestive tract of the patient.

45. The retrieving device of item 44, further comprising one or more features as defined in any one of items 2 to 38.

46. A method for retrieving a magnetic implant of a pair of magnetic implants configured for forming an anastomosis between two adjacent walls of a digestive tract of a patient, the method comprising:
navigating the magnetic implant into the digestive tract in direction of a location on one side of a desired anastomose site;
introducing a retrieving device into the digestive tract of the patient, a positioning of the retrieving device being modifiable by a healthcare provider via a delivery wire engaged with the retrieving device;
magnetically coupling the magnetic implant with the retrieving device; and
displacing the magnetic implant magnetically coupled with the retrieving device via the delivery wire along the digestive tract.

47. The method of item 46, wherein navigating the magnetic implant into the digestive tract in direction of a location on one side of a desired anastomose site is performed endoscopically, laparoscopically or percutaneously.

The invention claimed is:

1. A retrieving device for insertion within a digestive tract of a patient, the retrieving device comprising:
a flexible housing having a proximal portion engageable with a delivery wire and a distal portion opposite the proximal portion, the flexible housing comprising:
a housing wall defining a retriever magnet receiving cavity; and
a plurality of retriever magnets provided in series within the retriever magnet receiving cavity, the retriever magnets being distributed within the retriever magnet receiving cavity so as to define a non-magnetic portion and a magnetic portion of the retrieving device thereby enabling the retriever magnets of the plurality of retriever magnets to move freely and be subjected to a translational displacement in a longitudinal direction within the retriever magnet receiving cavity;

the retriever magnets having a diameter sized to define a displacement void between an outer surface of the retriever magnets and an inner surface of the housing wall of the flexible housing;

wherein the retrieving device is magnetically engageable with a first magnetic implant of a pair of magnetic implants configured for forming an anastomosis between two adjacent walls of the digestive tract of the patient.

2. The retrieving device of claim 1, wherein the housing wall of the flexible housing defines retriever housing slots extending laterally around a portion of the housing wall.

3. The retrieving device of claim 2, wherein longitudinally adjacent ones of the retriever housing slots are provided in an offset configuration.

4. The retrieving device of claim 1, wherein the flexible housing is tubular, and the housing wall of the flexible housing defines retriever housing slots extending circumferentially around a portion of the housing wall.

5. The retrieving device of claim 4, wherein the retriever housing slots comprise:

a first set of retriever housing slots provided spaced-apart from each other and extending along a first arc of the flexible housing; and a second set of retriever housing slots provided spaced-apart from each other and extending along a second arc of the flexible housing, the first and second sets of the retriever housing slots being longitudinally spaced-apart from one another.

6. The retrieving device of claim 5, wherein the first set of retriever housing slots comprises a first pair of retriever housing slots and the second set of retriever housing slots comprises a second pair retriever housing slots.

7. The retrieving device of claim 1, wherein the flexible housing comprises a flexible material.

8. The retrieving device of claim 7, wherein the flexible material comprises a polymeric material.

9. The retrieving device of claim 1, wherein the flexible housing comprises a non- flexible material.

10. The retrieving device of claim 9, wherein the non-flexible material comprises a metal.

11. The retrieving device of claim 1, wherein the flexible housing comprises a flexible joint.

12. The retrieving device of claim 11, wherein the flexible joint comprises a coil, is bellow-shaped or comprises a flexible material.

13. The retrieving device of claim 11, wherein the flexible housing comprises a first portion upstream of the flexible joint and a second portion downstream of the flexible joint, the flexible joint being provided in a central region of the flexible housing.

14. The retrieving device of claim 13, wherein at least one of the first and second portions of the flexible housing comprises a non-flexible material.

15. The retrieving device of claim 1, wherein the flexible housing is shaped a coil.

16. The retrieving device of claim 1, wherein the retriever magnets are shaped as substantially spherical beads or have a cylindrical shape.

17. The retrieving device of claim 1, further comprising a distal plug at the distal portion of the flexible housing, the distal plug being engageable with the distal portion of the flexible housing to maintain the plurality of retriever magnets within the retriever magnet receiving cavity.

18. The retrieving device of claim 1, further comprising a distal plug at a distal portion of the flexible housing, the distal plug being integral with the distal portion of the flexible housing to maintain the plurality of retriever magnets within the retriever magnet receiving cavity.

19. The retrieving device of claim 1, further comprising a proximal stopper at the proximal portion of the flexible housing, the proximal stopper being engageable with the proximal portion of the flexible housing to maintain the plurality of retriever magnets within the retriever magnet receiving cavity.

20. The retrieving device of claim 1, further comprising a proximal stopper at the proximal portion of the flexible housing, the proximal stopper being integral with the flexible housing to maintain the plurality of retriever magnets within the retriever magnet receiving cavity.

21. The retrieving device of claim 20, wherein the proximal stopper is engageable with the delivery wire, or the proximal stopper comprises a delivery attachment engageable with the delivery wire.

22. The retrieving device of claim 1, wherein the retrieving device is magnetically engageable with the first magnetic implant by contacting a main surface of the first magnetic implant.

* * * * *